(12) United States Patent
Wham et al.

(10) Patent No.: US 8,298,223 B2
(45) Date of Patent: Oct. 30, 2012

(54) METHOD AND SYSTEM FOR PROGRAMMING AND CONTROLLING AN ELECTROSURGICAL GENERATOR SYSTEM

(75) Inventors: Robert H Wham, Boulder, CO (US); Thomas A Sturm, Erie, CO (US); William D Faulkner, Boulder, CO (US)

(73) Assignee: Covidien AG (CH)

( * ) Notice: Subject to any disclaimer, the term of this patent is extended or adjusted under 35 U.S.C. 154(b) by 270 days.

(21) Appl. No.: 12/754,429

(22) Filed: Apr. 5, 2010

(65) Prior Publication Data
US 2010/0191233 A1 Jul. 29, 2010

Related U.S. Application Data

(62) Division of application No. 10/554,837, filed as application No. PCT/US2004/013443 on Apr. 30, 2004, now Pat. No. 7,722,601.

(60) Provisional application No. 60/466,954, filed on May 1, 2003.

(51) Int. Cl.
*A61B 18/04* (2006.01)
(52) U.S. Cl. .............. 606/33; 606/34; 606/35; 606/32
(58) Field of Classification Search .............. 606/32–52
See application file for complete search history.

(56) References Cited

U.S. PATENT DOCUMENTS

| | | |
|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 1,995,526 A | 3/1935 | Wappler |
| 2,827,056 A | 3/1958 | Degelman |
| 2,849,611 A | 8/1958 | Adams |
| 3,058,470 A | 10/1962 | Seeliger et al. |
| 3,089,496 A | 5/1963 | Degelman |
| 3,154,365 A | 10/1964 | Crimmins |
| 3,163,165 A | 12/1964 | Islikawa |
| 3,252,052 A | 5/1966 | Nash |
| 3,391,351 A | 7/1968 | Trent |
| 3,413,480 A | 11/1968 | Biard et al. |
| 3,436,563 A | 4/1969 | Regitz |

(Continued)

FOREIGN PATENT DOCUMENTS

DE 179607 3/1905

(Continued)

OTHER PUBLICATIONS

Canadian Office Action for corresponding Application No. 2,524,289 dated Apr. 6, 2011.

(Continued)

*Primary Examiner* — Linda Dvorak
*Assistant Examiner* — Amanda Scott

(57) ABSTRACT

A method and system are disclosed enabling configuration of a control system for an electrosurgical generator system for creating new surgical applications without changing the underlying software system. The programmable electrosurgical generator system has an RF output stage for outputting at least one RF operating waveform for performing an electrosurgical procedure. The programmable electrosurgical generator system includes an inner loop system to change at least one parameter of the at least one RF operating waveform; an outer loop system to provide at least one operating command to the inner loop system; and a configuration control system that modifies at least one of the inner and outer loop systems based on received data from a sensor module.

18 Claims, 4 Drawing Sheets

U.S. PATENT DOCUMENTS

| | | |
|---|---|---|
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Bierlein |
| 3,743,918 A | 7/1973 | Maitre |
| 3,766,434 A | 10/1973 | Sherman |
| 3,768,019 A | 10/1973 | Podowski |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,898,554 A | 8/1975 | Knudsen |
| 3,905,373 A | 9/1975 | Gonser |
| 3,908,176 A | 9/1975 | De Boer et al. |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 4,005,714 A | 2/1977 | Hilebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,204,549 A | 5/1980 | Paglione |
| 4,209,018 A | 6/1980 | Meinke et al. |
| 4,228,809 A | 10/1980 | Paglione |
| 4,229,714 A | 10/1980 | Yu |
| 4,231,372 A | 11/1980 | Newton |
| 4,232,676 A | 11/1980 | Herczog |
| 4,237,887 A | 12/1980 | Gosner |
| 4,281,373 A | 7/1981 | Mabille |
| 4,287,557 A | 9/1981 | Brehse |
| 4,296,413 A | 10/1981 | Milkovic |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,375,220 A | 3/1983 | Matvias |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,539 A | 1/1985 | Zenitani et al. |
| 4,494,541 A | 1/1985 | Archibald |
| 4,514,619 A | 4/1985 | Kugelman |
| 4,520,818 A | 6/1985 | Mickiewicz |
| 4,532,924 A | 8/1985 | Auth et al. |
| 4,534,347 A | 8/1985 | Taylor |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,572,190 A | 2/1986 | Azam et al. |
| 4,580,557 A | 4/1986 | Hertzmann |
| 4,582,057 A | 4/1986 | Auth et al. |
| 4,586,120 A | 4/1986 | Malik et al. |
| 4,590,934 A | 5/1986 | Malis et al. |
| 4,595,248 A | 6/1986 | Brown |
| 4,608,977 A | 9/1986 | Brown |
| 4,612,940 A | 9/1986 | Kasevich et al. |
| 4,615,330 A | 10/1986 | Nagasaki et al. |
| 4,630,218 A | 12/1986 | Hurley |
| 4,632,109 A | 12/1986 | Paterson |
| 4,632,127 A | 12/1986 | Sterzer |
| 4,632,128 A | 12/1986 | Paglione et al. |
| 4,638,436 A | 1/1987 | Badger et al. |
| 4,644,955 A | 2/1987 | Mioduski |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,672,980 A | 6/1987 | Turner |
| 4,691,703 A | 9/1987 | Auth et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,741,348 A | 5/1988 | Kikuchi et al. |
| 4,744,372 A | 5/1988 | Kikuchi et al. |
| 4,747,416 A | 5/1988 | Kikuchi et al. |
| 4,753,248 A | 6/1988 | Engler et al. |
| 4,754,757 A | 7/1988 | Feucht |
| 4,767,999 A | 8/1988 | VerPlanck |
| 4,768,969 A | 9/1988 | Bauer et al. |
| 4,785,829 A | 11/1988 | Convert et al. |
| 4,788,634 A | 11/1988 | Schlecht et al. |
| 4,805,621 A | 2/1989 | Heinze et al. |
| 4,815,479 A | 3/1989 | Carr |

| | | | | | |
|---|---|---|---|---|---|
| 4,818,954 A | 4/1989 | Flachenecker et al. | 5,300,070 A | 4/1994 | Gentelia |
| 4,827,927 A | 5/1989 | Newton | 5,304,917 A | 4/1994 | Somerville |
| 4,848,335 A | 7/1989 | Manes | 5,318,563 A | 6/1994 | Malis et al. |
| 4,860,745 A | 8/1989 | Farin et al. | 5,323,778 A | 6/1994 | Kandarpa et al. |
| 4,860,752 A | 8/1989 | Turner | 5,324,283 A | 6/1994 | Heckele |
| 4,860,770 A | 8/1989 | Kikuchi et al. | 5,330,518 A | 7/1994 | Neilson et al. |
| 4,862,889 A | 9/1989 | Feucht | 5,334,183 A | 8/1994 | Wuchinich |
| 4,873,995 A | 10/1989 | Kikuchi et al. | 5,334,193 A | 8/1994 | Nardella |
| 4,884,580 A | 12/1989 | Kikuchi et al. | 5,341,807 A | 8/1994 | Nardella |
| 4,887,199 A | 12/1989 | Whittle | 5,342,349 A | 8/1994 | Kaufman |
| 4,890,610 A | 1/1990 | Kirwan et al. | 5,342,356 A | 8/1994 | Ellman |
| 4,903,696 A | 2/1990 | Stasz et al. | 5,342,357 A | 8/1994 | Nardella |
| 4,907,589 A | 3/1990 | Cosman | 5,342,409 A | 8/1994 | Mullett |
| 4,922,210 A | 5/1990 | Flachenecker et al. | 5,344,435 A | 9/1994 | Turner et al. |
| 4,925,089 A | 5/1990 | Chaparro et al. | 5,346,406 A | 9/1994 | Hoffman et al. |
| 4,931,047 A | 6/1990 | Broadwin et al. | 5,346,491 A | 9/1994 | Oertli |
| 4,931,717 A | 6/1990 | Gray et al. | 5,348,554 A | 9/1994 | Imran et al. |
| 4,938,761 A | 7/1990 | Ensslin | 5,354,325 A | 10/1994 | Chive et al. |
| 4,942,313 A | 7/1990 | Kinzel | 5,364,392 A | 11/1994 | Warner et al. |
| 4,945,912 A | 8/1990 | Langberg | 5,369,567 A | 11/1994 | Furuta et al. |
| 4,955,377 A | 9/1990 | Lennox et al. | 5,370,645 A | 12/1994 | Klicek et al. |
| 4,959,606 A | 9/1990 | Forge | 5,370,672 A | 12/1994 | Fowler et al. |
| 4,961,047 A | 10/1990 | Carder | 5,370,675 A | 12/1994 | Edwards et al. |
| 4,961,435 A | 10/1990 | Kitagawa et al. | 5,372,596 A | 12/1994 | Klicek et al. |
| 4,966,597 A | 10/1990 | Cosman | 5,383,874 A | 1/1995 | Jackson et al. |
| 4,967,765 A | 11/1990 | Turner et al. | 5,383,876 A | 1/1995 | Nardella |
| 4,969,885 A | 11/1990 | Farin | 5,383,917 A | 1/1995 | Desai et al. |
| 4,992,719 A | 2/1991 | Harvey | 5,385,148 A | 1/1995 | Lesh et al. |
| 4,993,430 A | 2/1991 | Shimoyama et al. | 5,400,267 A | 3/1995 | Denen et al. |
| 4,995,877 A | 2/1991 | Ams et al. | 5,403,311 A | 4/1995 | Abele et al. |
| 5,015,227 A | 5/1991 | Broadwin et al. | 5,403,312 A | 4/1995 | Yates et al. |
| 5,019,076 A | 5/1991 | Yamanashi et al. | 5,405,346 A | 4/1995 | Grundy et al. |
| 5,024,668 A | 6/1991 | Peters et al. | 5,409,000 A | 4/1995 | Imran |
| 5,025,810 A | 6/1991 | Kikuchi et al. | 5,409,485 A | 4/1995 | Suda |
| 5,033,478 A | 7/1991 | Kikuchi et al. | 5,413,573 A | 5/1995 | Koivukangas |
| 5,044,977 A | 9/1991 | Vindigni | 5,414,238 A | 5/1995 | Steigerwald et al. |
| 5,057,106 A | 10/1991 | Kasevich et al. | 5,417,719 A | 5/1995 | Hull et al. |
| 5,067,953 A | 11/1991 | Feucht | 5,422,567 A | 6/1995 | Matsunaga |
| 5,075,839 A | 12/1991 | Fisher et al. | 5,422,926 A | 6/1995 | Smith et al. |
| 5,087,257 A | 2/1992 | Farin | 5,423,808 A | 6/1995 | Edwards et al. |
| 5,099,840 A | 3/1992 | Goble et al. | 5,423,809 A | 6/1995 | Klicek |
| 5,103,804 A | 4/1992 | Abele et al. | 5,423,810 A | 6/1995 | Goble et al. |
| 5,108,389 A | 4/1992 | Cosmescu | 5,423,811 A | 6/1995 | Imran et al. |
| 5,108,391 A | 4/1992 | Flachenecker | 5,425,704 A | 6/1995 | Sakurai et al. |
| 5,119,284 A | 6/1992 | Fisher et al. | 5,429,596 A | 7/1995 | Arias et al. |
| 5,122,137 A | 6/1992 | Lennox | 5,430,434 A | 7/1995 | Lederer et al. |
| 5,133,711 A | 7/1992 | Hagen | 5,432,459 A | 7/1995 | Thompson |
| 5,148,814 A | 9/1992 | Kikuchi et al. | 5,433,739 A | 7/1995 | Sluijter et al. |
| 5,151,102 A | 9/1992 | Kamiyama et al. | 5,433,740 A | 7/1995 | Yamaguchi |
| 5,152,762 A | 10/1992 | McElhenney | 5,436,566 A | 7/1995 | Thompson |
| 5,157,603 A | 10/1992 | Scheller et al. | 5,438,302 A | 8/1995 | Goble |
| 5,160,334 A | 11/1992 | Billings et al. | 5,443,462 A | 8/1995 | Hannant |
| 5,161,893 A | 11/1992 | Shigezawa et al. | 5,443,463 A | 8/1995 | Stern et al. |
| 5,167,658 A | 12/1992 | Ensslin | 5,445,635 A | 8/1995 | Denen |
| 5,167,659 A | 12/1992 | Ohtomo et al. | 5,451,224 A | 9/1995 | Goble et al. |
| 5,190,517 A | 3/1993 | Zieve et al. | 5,452,725 A | 9/1995 | Martenson |
| 5,196,008 A | 3/1993 | Kuenecke | 5,454,809 A | 10/1995 | Janssen |
| 5,196,009 A | 3/1993 | Kirwan, Jr. | 5,458,597 A | 10/1995 | Edwards et al. |
| 5,201,900 A | 4/1993 | Nardella | 5,462,521 A | 10/1995 | Brucker et al. |
| 5,207,691 A | 5/1993 | Nardella | 5,472,441 A | 12/1995 | Edwards et al. |
| 5,211,570 A | 5/1993 | Bitney | 5,472,443 A | 12/1995 | Cordis et al. |
| 5,220,927 A | 6/1993 | Astrahan et al. | 5,474,464 A | 12/1995 | Drewnicki |
| 5,230,623 A | 7/1993 | Guthrie et al. | 5,480,399 A | 1/1996 | Hebborn |
| 5,233,515 A | 8/1993 | Cosman | 5,483,952 A | 1/1996 | Aranyi |
| 5,234,004 A | 8/1993 | Hascoet et al. | 5,496,312 A | 3/1996 | Klicek |
| 5,234,427 A | 8/1993 | Ohtomo et al. | 5,496,313 A | 3/1996 | Gentelia et al. |
| 5,249,121 A | 9/1993 | Baum et al. | 5,496,314 A | 3/1996 | Eggers |
| 5,249,585 A | 10/1993 | Turner et al. | 5,500,012 A | 3/1996 | Brucker et al. |
| 5,254,117 A | 10/1993 | Rigby et al. | 5,500,616 A | 3/1996 | Ochi |
| RE34,432 E | 11/1993 | Bertrand | 5,511,993 A | 4/1996 | Yamada et al. |
| 5,267,994 A | 12/1993 | Gentelia et al. | 5,514,129 A | 5/1996 | Smith |
| 5,267,997 A | 12/1993 | Farin | 5,520,684 A | 5/1996 | Imran |
| 5,275,597 A | 1/1994 | Higgins et al. | 5,531,774 A | 7/1996 | Schulman et al. |
| 5,281,213 A | 1/1994 | Milder et al. | 5,534,018 A | 7/1996 | Wahlstrand et al. |
| 5,282,840 A | 2/1994 | Hudrlik | 5,536,267 A | 7/1996 | Edwards et al. |
| 5,290,283 A | 3/1994 | Suda | 5,540,677 A | 7/1996 | Sinofsky |
| 5,295,857 A | 3/1994 | Toly | 5,540,681 A * | 7/1996 | Strul et al. ............... 606/34 |
| 5,295,955 A | 3/1994 | Rosen et al. | 5,540,682 A | 7/1996 | Gardner et al. |
| 5,300,068 A | 4/1994 | Rosar et al. | 5,540,683 A | 7/1996 | Ichikawa |

| | | | | | |
|---|---|---|---|---|---|
| 5,540,684 A | 7/1996 | Hassler, Jr. | 5,827,271 A | 10/1998 | Bussey et al. |
| 5,541,376 A | 7/1996 | Ladtkow et al. | 5,830,212 A | 11/1998 | Cartmell |
| 5,545,161 A | 8/1996 | Imran | 5,836,909 A | 11/1998 | Cosmescu |
| 5,556,396 A | 9/1996 | Cohen et al. | 5,836,943 A | 11/1998 | Miller, III |
| 5,558,671 A | 9/1996 | Yates | 5,836,990 A | 11/1998 | Li |
| 5,562,720 A | 10/1996 | Stern et al. | 5,843,019 A | 12/1998 | Eggers et al. |
| 5,569,242 A | 10/1996 | Lax et al. | 5,843,075 A | 12/1998 | Taylor |
| 5,571,098 A | 11/1996 | Domankevitz et al. | 5,846,236 A | 12/1998 | Lindenmeier et al. |
| 5,571,147 A | 11/1996 | Sluijter et al. | 5,849,010 A | 12/1998 | Wurzer et al. |
| 5,571,154 A | 11/1996 | Ren | 5,853,409 A | 12/1998 | Swanson et al. |
| 5,573,533 A | 11/1996 | Strul | 5,860,832 A | 1/1999 | Wayt et al. |
| 5,584,830 A | 12/1996 | Ladd et al. | 5,865,788 A | 2/1999 | Edwards et al. |
| 5,588,432 A | 12/1996 | Crowley | 5,868,737 A | 2/1999 | Taylor et al. |
| 5,596,466 A | 1/1997 | Ochi | 5,868,739 A | 2/1999 | Lindenmeier et al. |
| 5,599,344 A | 2/1997 | Paterson | 5,868,740 A | 2/1999 | LeVeen et al. |
| 5,599,345 A | 2/1997 | Edwards et al. | 5,871,481 A | 2/1999 | Kannenberg et al. |
| 5,599,348 A | 2/1997 | Gentelia et al. | 5,891,142 A | 4/1999 | Eggers et al. |
| 5,605,150 A | 2/1997 | Radons et al. | 5,893,848 A | 4/1999 | Negus et al. |
| 5,609,560 A | 3/1997 | Ichikawa et al. | 5,897,552 A | 4/1999 | Edwards et al. |
| 5,613,966 A | 3/1997 | Makower et al. | 5,904,709 A | 5/1999 | Arndt et al. |
| 5,620,480 A | 4/1997 | Rudie | 5,906,614 A | 5/1999 | Stern et al. |
| 5,620,481 A | 4/1997 | Desai et al. | 5,908,444 A | 6/1999 | Azure |
| 5,626,575 A | 5/1997 | Crenner | 5,913,882 A | 6/1999 | King |
| 5,628,745 A | 5/1997 | Bek | 5,921,982 A | 7/1999 | Lesh et al. |
| 5,628,771 A | 5/1997 | Mizukawa et al. | 5,922,013 A | 7/1999 | Fallik |
| 5,643,330 A | 7/1997 | Holsheimer et al. | 5,925,070 A | 7/1999 | King et al. |
| 5,647,869 A | 7/1997 | Goble et al. | 5,931,836 A | 8/1999 | Hatta et al. |
| 5,647,871 A | 7/1997 | Levine et al. | 5,935,124 A | 8/1999 | Klumb et al. |
| 5,651,780 A | 7/1997 | Jackson et al. | 5,938,690 A | 8/1999 | Law et al. |
| 5,658,322 A | 8/1997 | Fleming | 5,944,022 A | 8/1999 | Nardella et al. |
| 5,660,567 A | 8/1997 | Nierlich et al. | 5,944,553 A | 8/1999 | Yasui et al. |
| 5,664,953 A | 9/1997 | Reylek | 5,948,007 A | 9/1999 | Starkebaum et al. |
| 5,674,217 A | 10/1997 | Wahlstrom et al. | 5,951,545 A | 9/1999 | Schilling |
| 5,678,568 A | 10/1997 | Uchikubo et al. | 5,951,546 A | 9/1999 | Lorentzen |
| 5,681,307 A | 10/1997 | McMahan | 5,954,686 A | 9/1999 | Garito et al. |
| 5,685,840 A | 11/1997 | Schechter et al. | 5,954,717 A | 9/1999 | Behl et al. |
| 5,688,267 A | 11/1997 | Panescu et al. | 5,954,719 A | 9/1999 | Chen et al. |
| 5,693,042 A | 12/1997 | Bioarski et al. | 5,957,961 A | 9/1999 | Maguire et al. |
| 5,693,078 A | 12/1997 | Desai et al. | 5,957,969 A | 9/1999 | Warner et al. |
| 5,693,082 A | 12/1997 | Warner et al. | 5,959,253 A | 9/1999 | Shinchi |
| 5,694,304 A | 12/1997 | Telefus et al. | 5,961,344 A | 10/1999 | Rosales et al. |
| 5,695,494 A | 12/1997 | Becker | 5,961,871 A | 10/1999 | Bible et al. |
| 5,696,441 A | 12/1997 | Mak et al. | 5,964,746 A | 10/1999 | McCary |
| 5,697,925 A | 12/1997 | Taylor | 5,967,976 A | 10/1999 | Larsen et al. |
| 5,697,927 A | 12/1997 | Imran et al. | 5,971,980 A | 10/1999 | Sherman |
| 5,702,386 A | 12/1997 | Stern et al. | 5,971,981 A | 10/1999 | Hill et al. |
| 5,702,429 A | 12/1997 | King | 5,976,128 A | 11/1999 | Schilling et al. |
| 5,707,369 A | 1/1998 | Vaitekunas et al. | 5,983,141 A | 11/1999 | Sluijter et al. |
| 5,712,772 A | 1/1998 | Telefus et al. | 6,007,532 A | 12/1999 | Netherly |
| 5,713,896 A | 2/1998 | Nardella | 6,010,499 A | 1/2000 | Cobb |
| 5,718,246 A | 2/1998 | Vona | 6,013,074 A | 1/2000 | Taylor |
| 5,720,742 A | 2/1998 | Zacharias | 6,014,581 A | 1/2000 | Whayne et al. |
| 5,720,744 A | 2/1998 | Eggleston et al. | 6,016,452 A | 1/2000 | Kasevich |
| 5,722,975 A | 3/1998 | Edwards et al. | 6,017,338 A | 1/2000 | Brucker et al. |
| 5,729,448 A | 3/1998 | Haynie et al. | 6,017,354 A | 1/2000 | Culp et al. |
| 5,733,281 A | 3/1998 | Nardella | 6,019,757 A | 2/2000 | Scheldrup |
| 5,735,846 A | 4/1998 | Panescu et al. | 6,022,346 A | 2/2000 | Panescu et al. |
| 5,738,683 A | 4/1998 | Osypka | 6,022,347 A | 2/2000 | Lindenmeier et al. |
| 5,743,900 A | 4/1998 | Hara | 6,032,078 A | 2/2000 | Rudie |
| 5,743,903 A | 4/1998 | Stern et al. | 6,033,399 A | 3/2000 | Gines |
| 5,749,869 A | 5/1998 | Lindenmeier et al. | 6,039,731 A | 3/2000 | Taylor et al. |
| 5,749,871 A | 5/1998 | Hood et al. | 6,039,732 A | 3/2000 | Ichikawa et al. |
| 5,755,715 A | 5/1998 | Stern | 6,041,260 A | 3/2000 | Stern et al. |
| 5,762,609 A | 6/1998 | Benaron et al. | 6,044,283 A | 3/2000 | Fein et al. |
| 5,766,153 A | 6/1998 | Eggers et al. | 6,047,216 A | 4/2000 | Carl et al. |
| 5,766,165 A | 6/1998 | Gentelia et al. | 6,053,910 A | 4/2000 | Fleenor |
| 5,769,847 A | 6/1998 | Panescu | 6,053,912 A | 4/2000 | Panescu et al. |
| 5,772,659 A | 6/1998 | Becker et al. | 6,055,458 A | 4/2000 | Cochran et al. |
| 5,788,688 A | 8/1998 | Bauer et al. | 6,056,745 A | 5/2000 | Panescu et al. |
| 5,792,138 A | 8/1998 | Shipp | 6,056,746 A | 5/2000 | Goble et al. |
| 5,797,902 A | 8/1998 | Netherly | 6,059,781 A | 5/2000 | Yamanashi et al. |
| 5,797,941 A | 8/1998 | Schulze et al. | 6,063,075 A | 5/2000 | Mihori |
| 5,800,494 A | 9/1998 | Campbell et al. | 6,063,078 A | 5/2000 | Wittkampf |
| 5,807,253 A | 9/1998 | Dumoulin et al. | 6,066,137 A | 5/2000 | Greep |
| 5,810,804 A | 9/1998 | Gough et al. | 6,067,475 A | 5/2000 | Graves et al. |
| 5,814,092 A | 9/1998 | King | 6,068,627 A | 5/2000 | Orszulak et al. |
| 5,817,091 A | 10/1998 | Nardella et al. | 6,074,089 A | 6/2000 | Hollander et al. |
| 5,817,093 A | 10/1998 | Williamson, IV et al. | 6,074,386 A | 6/2000 | Goble et al. |
| 5,820,568 A | 10/1998 | Willis | 6,074,388 A | 6/2000 | Tockweiler et al. |

| | | | |
|---|---|---|---|
| 6,080,149 A | 6/2000 | Huang et al. | |
| 6,088,614 A | 7/2000 | Swanson | |
| 6,090,123 A | 7/2000 | Culp et al. | |
| 6,093,186 A | 7/2000 | Goble | |
| 6,097,985 A | 8/2000 | Kasevich et al. | |
| 6,102,497 A | 8/2000 | Ehr et al. | |
| 6,102,907 A | 8/2000 | Smethers et al. | |
| 6,106,520 A | 8/2000 | Laufer et al. | |
| 6,106,524 A | 8/2000 | Eggers et al. | |
| 6,113,591 A | 9/2000 | Whayne et al. | |
| 6,113,592 A | 9/2000 | Taylor | |
| 6,113,593 A | 9/2000 | Tu et al. | |
| 6,113,596 A | 9/2000 | Hooven | |
| 6,122,551 A | 9/2000 | Rudie et al. | |
| 6,123,701 A | 9/2000 | Nezhat | |
| 6,123,702 A | 9/2000 | Swanson et al. | |
| 6,132,429 A | 10/2000 | Baker | |
| 6,134,476 A | 10/2000 | Arndt et al. | |
| 6,136,020 A | 10/2000 | Faour | |
| 6,142,992 A | 11/2000 | Cheng et al. | |
| 6,155,975 A | 12/2000 | Urich et al. | |
| 6,161,048 A | 12/2000 | Sluijter et al. | |
| 6,162,184 A | 12/2000 | Swanson et al. | |
| 6,162,217 A | 12/2000 | Kannenberg et al. | |
| 6,163,726 A | 12/2000 | Wolf | |
| 6,165,169 A | 12/2000 | Panescu et al. | |
| 6,167,313 A | 12/2000 | Gray et al. | |
| 6,171,304 B1 | 1/2001 | Netherly et al. | |
| 6,175,768 B1 | 1/2001 | Arndt et al. | |
| 6,179,832 B1 | 1/2001 | Jones et al. | |
| 6,181,970 B1 | 1/2001 | Kasevich | |
| 6,183,468 B1 | 2/2001 | Swanson et al. | |
| 6,186,147 B1 | 2/2001 | Cobb | |
| 6,188,211 B1 | 2/2001 | Rincon-Mora et al. | |
| 6,188,930 B1 | 2/2001 | Carson | |
| 6,193,713 B1 | 2/2001 | Geistert et al. | |
| 6,197,023 B1 | 3/2001 | Muntermann | |
| 6,203,541 B1 | 3/2001 | Keppel | |
| 6,210,403 B1 | 4/2001 | Klicek | |
| 6,216,703 B1 | 4/2001 | Manker et al. | |
| 6,216,704 B1 | 4/2001 | Ingle et al. | |
| 6,222,356 B1 | 4/2001 | Taghizadeh-Kaschani | |
| 6,226,553 B1 | 5/2001 | Carl et al. | |
| 6,228,078 B1 | 5/2001 | Eggers et al. | |
| 6,228,079 B1 | 5/2001 | Koenig | |
| 6,228,080 B1 | 5/2001 | Gines | |
| 6,228,081 B1 | 5/2001 | Goble | |
| 6,231,569 B1 | 5/2001 | Bek | |
| 6,232,556 B1 | 5/2001 | Daugherty et al. | |
| 6,233,490 B1 | 5/2001 | Kasevich | |
| 6,235,020 B1 | 5/2001 | Cheng et al. | |
| 6,235,022 B1 | 5/2001 | Hallock et al. | |
| 6,237,604 B1 | 5/2001 | Burnside et al. | |
| 6,238,387 B1 | 5/2001 | Miller, III | |
| 6,238,388 B1 | 5/2001 | Ellman | |
| 6,241,723 B1 | 6/2001 | Heim et al. | |
| 6,241,725 B1 | 6/2001 | Cosman | |
| 6,243,654 B1 | 6/2001 | Johnson et al. | |
| 6,245,061 B1 | 6/2001 | Panescu et al. | |
| 6,245,063 B1 | 6/2001 | Uphoff | |
| 6,245,065 B1 | 6/2001 | Panescu | |
| 6,246,912 B1 | 6/2001 | Sluijter et al. | |
| 6,251,106 B1 | 6/2001 | Becker et al. | |
| 6,251,128 B1 | 6/2001 | Knopp et al. | |
| 6,254,422 B1 | 7/2001 | Feye-Hohmann | |
| 6,258,085 B1 | 7/2001 | Eggleston | |
| 6,261,285 B1 | 7/2001 | Novak | |
| 6,261,286 B1 | 7/2001 | Goble et al. | |
| 6,267,760 B1 | 7/2001 | Swanson | |
| 6,272,384 B1 | 8/2001 | Simon et al. | |
| 6,273,886 B1 | 8/2001 | Edwards et al. | |
| 6,275,738 B1 | 8/2001 | Kasevich et al. | |
| 6,275,786 B1 | 8/2001 | Daners | |
| 6,289,249 B1 | 9/2001 | Arndt et al. | |
| 6,293,941 B1 | 9/2001 | Strul et al. | |
| 6,293,942 B1 | 9/2001 | Goble et al. | |
| 6,293,943 B1 | 9/2001 | Panescu et al. | |
| 6,296,636 B1 | 10/2001 | Cheng et al. | |
| 6,306,131 B1 | 10/2001 | Hareyama et al. | |
| 6,306,134 B1 | 10/2001 | Goble et al. | |
| 6,309,386 B1 | 10/2001 | Bek | |
| 6,312,391 B1 | 11/2001 | Ramadhyani et al. | |
| 6,322,558 B1 | 11/2001 | Taylor et al. | |
| 6,325,799 B1 | 12/2001 | Goble | |
| 6,329,778 B1 | 12/2001 | Culp et al. | |
| 6,334,074 B1 | 12/2001 | Spertell | |
| 6,337,998 B1 | 1/2002 | Behl et al. | |
| 6,338,657 B1 | 1/2002 | Harper et al. | |
| 6,347,251 B1 | 2/2002 | Deng | |
| 6,350,262 B1 | 2/2002 | Ashley | |
| 6,358,245 B1 | 3/2002 | Edwards | |
| 6,364,877 B1 | 4/2002 | Goble et al. | |
| 6,366,818 B1 | 4/2002 | Bolmsjo | |
| 6,370,408 B1 | 4/2002 | Merchant et al. | |
| 6,371,963 B1 | 4/2002 | Nishtala et al. | |
| 6,380,815 B1 | 4/2002 | Fehrenbach et al. | |
| 6,383,183 B1 | 5/2002 | Sekino et al. | |
| 6,391,024 B1 | 5/2002 | Sun et al. | |
| 6,398,779 B1 * | 6/2002 | Buysse et al. | 606/34 |
| 6,398,781 B1 | 6/2002 | Goble et al. | |
| 6,402,741 B1 | 6/2002 | Keppel et al. | |
| 6,402,742 B1 | 6/2002 | Blewett et al. | |
| 6,402,743 B1 | 6/2002 | Orszulak et al. | |
| 6,402,748 B1 | 6/2002 | Schoenman et al. | |
| 6,409,722 B1 | 6/2002 | Hoey et al. | |
| 6,413,256 B1 | 7/2002 | Truckai et al. | |
| 6,416,509 B1 | 7/2002 | Goble et al. | |
| 6,422,896 B2 | 7/2002 | Aoki et al. | |
| 6,423,057 B1 | 7/2002 | He et al. | |
| 6,426,886 B1 | 7/2002 | Goder | |
| 6,428,537 B1 | 8/2002 | Swanson et al. | |
| 6,430,446 B1 | 8/2002 | Knowlton | |
| 6,436,096 B1 | 8/2002 | Hareyama | |
| 6,440,157 B1 | 8/2002 | Shigezawa et al. | |
| 6,451,015 B1 | 9/2002 | Rittman, III et al. | |
| 6,454,594 B2 | 9/2002 | Sawayanagi | |
| 6,458,121 B1 | 10/2002 | Rosenstock | |
| 6,458,122 B1 | 10/2002 | Pozzato | |
| 6,464,689 B1 | 10/2002 | Qin | |
| 6,464,696 B1 | 10/2002 | Oyama | |
| 6,468,270 B1 | 10/2002 | Hovda et al. | |
| 6,468,273 B1 | 10/2002 | Leveen et al. | |
| 6,470,217 B1 | 10/2002 | Fenn et al. | |
| 6,477,426 B1 | 11/2002 | Fenn et al. | |
| 6,482,201 B1 | 11/2002 | Olsen et al. | |
| 6,485,486 B1 | 11/2002 | Trembly et al. | |
| 6,488,678 B2 | 12/2002 | Sherman | |
| 6,490,488 B1 | 12/2002 | Rudie et al. | |
| 6,494,880 B1 | 12/2002 | Swanson et al. | |
| 6,496,736 B1 | 12/2002 | Carl et al. | |
| 6,496,738 B2 | 12/2002 | Carr | |
| 6,497,659 B1 | 12/2002 | Rafert | |
| 6,498,466 B1 | 12/2002 | Edwards | |
| 6,503,191 B1 | 1/2003 | Miller | |
| 6,506,189 B1 | 1/2003 | Rittman, III et al. | |
| 6,508,815 B1 | 1/2003 | Strul | |
| 6,511,476 B2 | 1/2003 | Hareyama | |
| 6,511,478 B1 | 1/2003 | Burnside | |
| 6,512,956 B2 | 1/2003 | Arndt et al. | |
| 6,517,538 B1 | 2/2003 | Jacob et al. | |
| 6,522,931 B2 | 2/2003 | Manker et al. | |
| 6,524,308 B1 | 2/2003 | Muller et al. | |
| 6,526,320 B2 | 2/2003 | Mitchell | |
| 6,537,272 B2 | 3/2003 | Christopherson et al. | |
| 6,542,767 B1 | 4/2003 | McNichols et al. | |
| 6,544,260 B1 | 4/2003 | Markel et al. | |
| 6,546,270 B1 | 4/2003 | Goldin et al. | |
| 6,547,786 B1 | 4/2003 | Goble | |
| 6,557,559 B1 | 5/2003 | Eggers et al. | |
| 6,558,376 B2 | 5/2003 | Bishop | |
| 6,558,377 B2 | 5/2003 | Lee et al. | |
| 6,560,470 B1 | 5/2003 | Pologe | |
| 6,562,037 B2 | 5/2003 | Paton | |
| 6,565,559 B2 | 5/2003 | Eggleston | |
| 6,565,562 B1 | 5/2003 | Shah et al. | |
| 6,575,969 B1 | 6/2003 | Rittman, III et al. | |
| 6,578,579 B2 | 6/2003 | Burnside et al. | |
| 6,579,288 B1 | 6/2003 | Swanson et al. | |

| | | |
|---|---|---|
| 6,582,425 B2 | 6/2003 | Simpson |
| 6,582,427 B1 | 6/2003 | Goble et al. |
| 6,592,579 B2 | 7/2003 | Arndt et al. |
| 6,602,243 B2 | 8/2003 | Noda |
| 6,602,252 B2 | 8/2003 | Mollenauer |
| 6,611,793 B1 | 8/2003 | Burnside et al. |
| 6,620,157 B1 | 9/2003 | Dabney et al. |
| 6,620,189 B1 | 9/2003 | Machold et al. |
| 6,623,423 B2 | 9/2003 | Sakurai |
| 6,626,901 B1 | 9/2003 | Treat et al. |
| 6,628,990 B1 | 9/2003 | Habib et al. |
| 6,629,973 B1 | 10/2003 | Wardell et al. |
| 6,632,193 B1 | 10/2003 | Davison et al. |
| 6,635,056 B2 | 10/2003 | Kadhiresan et al. |
| 6,635,057 B2 | 10/2003 | Harano |
| 6,640,139 B1 | 10/2003 | Ueberle |
| 6,645,198 B1 | 11/2003 | Bommannan et al. |
| 6,648,883 B2 | 11/2003 | Francischelli |
| 6,651,669 B1 | 11/2003 | Burnside |
| 6,652,513 B2 | 11/2003 | Panescu et al. |
| 6,652,514 B2 | 11/2003 | Ellman |
| 6,653,569 B1 | 11/2003 | Sung |
| 6,656,177 B2 | 12/2003 | Truckai et al. |
| 6,663,623 B1 | 12/2003 | Oyama et al. |
| 6,663,624 B2 | 12/2003 | Edwards et al. |
| 6,663,627 B2 | 12/2003 | Francischelli et al. |
| 6,666,860 B1 | 12/2003 | Takahashi |
| 6,666,862 B2 | 12/2003 | Jain et al. |
| 6,671,535 B1 | 12/2003 | McNichols et al. |
| 6,672,151 B1 | 1/2004 | Schultz et al. |
| 6,675,050 B2 | 1/2004 | Arndt et al. |
| 6,679,875 B2 | 1/2004 | Honda |
| 6,682,527 B2 | 1/2004 | Strul |
| 6,685,700 B2 | 2/2004 | Behl |
| 6,685,701 B2 | 2/2004 | Orszulak et al. |
| 6,685,703 B2 | 2/2004 | Pearson et al. |
| 6,689,131 B2 | 2/2004 | McClurken |
| 6,690,976 B2 | 2/2004 | Fenn et al. |
| 6,692,489 B1 | 2/2004 | Heim |
| 6,693,782 B1 | 2/2004 | Lash |
| 6,695,837 B2 | 2/2004 | Howell |
| 6,696,844 B2 | 2/2004 | Wong et al. |
| 6,712,813 B2 | 3/2004 | Ellman |
| 6,723,091 B2 * | 4/2004 | Goble et al. .................... 606/41 |
| 6,725,095 B2 | 4/2004 | Fenn et al. |
| 6,730,078 B2 | 5/2004 | Simpson et al. |
| 6,730,079 B2 | 5/2004 | Lovewell |
| 6,730,080 B2 | 5/2004 | Harano |
| 6,733,495 B1 | 5/2004 | Bek |
| 6,733,498 B2 | 5/2004 | Paton |
| 6,740,079 B1 | 5/2004 | Eggers |
| 6,740,085 B2 | 5/2004 | Hareyama |
| 6,743,225 B2 | 6/2004 | Sanchez et al. |
| 6,746,284 B1 | 6/2004 | Spink, Jr. |
| 6,749,624 B2 | 6/2004 | Knowlton |
| 6,752,804 B2 | 6/2004 | Simpson et al. |
| 6,755,825 B2 | 6/2004 | Shoenman et al. |
| 6,758,846 B2 | 7/2004 | Goble et al. |
| 6,761,716 B2 | 7/2004 | Kadhiresan et al. |
| 6,771,139 B2 | 8/2004 | Schultheiss et al. |
| 6,778,044 B2 | 8/2004 | Fehrenbach et al. |
| 6,783,523 B2 | 8/2004 | Qin |
| 6,784,405 B2 | 8/2004 | Flugstad et al. |
| 6,786,905 B2 | 9/2004 | Swanson et al. |
| 6,788,977 B2 | 9/2004 | Fenn et al. |
| 6,790,206 B2 | 9/2004 | Panescu |
| 6,792,390 B1 | 9/2004 | Burnside et al. |
| 6,796,980 B2 | 9/2004 | Hall |
| 6,796,981 B2 | 9/2004 | Wham |
| 6,809,508 B2 | 10/2004 | Donofrio |
| 6,818,000 B2 | 11/2004 | Muller et al. |
| 6,823,218 B2 | 11/2004 | Berube |
| 6,824,539 B2 | 11/2004 | Novak |
| 6,830,569 B2 | 12/2004 | Thompson |
| 6,837,888 B2 | 1/2005 | Ciarrocca et al. |
| 6,843,682 B2 | 1/2005 | Matsuda et al. |
| 6,843,789 B2 | 1/2005 | Goble |
| 6,847,848 B2 | 1/2005 | Sterzer et al. |
| 6,849,073 B2 | 2/2005 | Hoey |
| 6,855,141 B2 | 2/2005 | Lovewell |
| 6,855,142 B2 | 2/2005 | Harano |
| 6,860,881 B2 | 3/2005 | Sturm |
| 6,864,686 B2 | 3/2005 | Novak |
| 6,866,624 B2 | 3/2005 | Chornenky et al. |
| 6,875,210 B2 | 4/2005 | Refior |
| 6,890,331 B2 | 5/2005 | Kristensen |
| 6,893,435 B2 | 5/2005 | Goble |
| 6,899,538 B2 | 5/2005 | Matoba |
| 6,923,804 B2 | 8/2005 | Eggers et al. |
| 6,929,641 B2 | 8/2005 | Goble et al. |
| 6,936,047 B2 | 8/2005 | Nasab et al. |
| 6,939,344 B2 | 9/2005 | Kreindel |
| 6,939,346 B2 | 9/2005 | Kannenberg et al. |
| 6,939,347 B2 | 9/2005 | Thompson |
| 6,939,348 B2 | 9/2005 | Malecki et al. |
| 6,942,660 B2 | 9/2005 | Pantera et al. |
| 6,944,504 B1 | 9/2005 | Arndt et al. |
| 6,948,503 B2 | 9/2005 | Refior et al. |
| 6,953,461 B2 | 10/2005 | McClurken et al. |
| 6,955,675 B2 | 10/2005 | Jain |
| 6,957,108 B2 | 10/2005 | Turner et al. |
| 6,958,064 B2 | 10/2005 | Rioux et al. |
| 6,962,586 B2 | 11/2005 | Berube et al. |
| 6,962,587 B2 | 11/2005 | Johnson et al. |
| 6,966,907 B2 | 11/2005 | Goble |
| 6,970,752 B1 | 11/2005 | Lim et al. |
| 6,974,453 B2 | 12/2005 | Woloszko et al. |
| 6,974,463 B2 | 12/2005 | Magers et al. |
| 6,977,495 B2 | 12/2005 | Donofrio |
| 6,984,231 B2 | 1/2006 | Goble et al. |
| 6,986,764 B2 | 1/2006 | Davenport et al. |
| 6,986,770 B2 | 1/2006 | Hood |
| 6,989,010 B2 | 1/2006 | Francischelli et al. |
| 6,994,704 B2 | 2/2006 | Qin et al. |
| 6,994,707 B2 | 2/2006 | Ellman et al. |
| 7,001,379 B2 | 2/2006 | Behl et al. |
| 7,001,381 B2 | 2/2006 | Harano et al. |
| 7,004,174 B2 | 2/2006 | Eggers et al. |
| 7,008,369 B2 | 3/2006 | Cuppen |
| 7,008,417 B2 | 3/2006 | Eick |
| 7,008,421 B2 | 3/2006 | Daniel et al. |
| 7,025,764 B2 | 4/2006 | Paton et al. |
| 7,033,351 B2 | 4/2006 | Howell |
| 7,041,096 B2 | 5/2006 | Malis et al. |
| 7,044,948 B2 | 5/2006 | Keppel |
| 7,044,949 B2 | 5/2006 | Orszulak et al. |
| 7,048,687 B1 | 5/2006 | Reuss et al. |
| 7,060,063 B2 | 6/2006 | Marion et al. |
| 7,062,331 B2 | 6/2006 | Zarinetchi et al. |
| 7,063,692 B2 | 6/2006 | Sakurai et al. |
| 7,066,933 B2 | 6/2006 | Hagg |
| 7,074,217 B2 | 7/2006 | Strul et al. |
| 7,083,618 B2 | 8/2006 | Couture et al. |
| 7,089,064 B2 | 8/2006 | Manker et al. |
| 7,093,601 B2 | 8/2006 | Manker et al. |
| 7,094,231 B1 | 8/2006 | Ellman et al. |
| 7,104,834 B2 | 9/2006 | Robinson et al. |
| 7,105,011 B2 | 9/2006 | Auge, II |
| 7,113,832 B2 | 9/2006 | Longo |
| RE39,358 E | 10/2006 | Goble |
| 7,115,121 B2 | 10/2006 | Novak |
| 7,115,124 B1 | 10/2006 | Xiao |
| 7,115,126 B2 | 10/2006 | Berube et al. |
| 7,118,564 B2 | 10/2006 | Ritchie et al. |
| 7,122,031 B2 | 10/2006 | Edwards et al. |
| 7,131,445 B2 | 11/2006 | Amoah |
| 7,131,860 B2 | 11/2006 | Sartor et al. |
| 7,137,980 B2 | 11/2006 | Buysse et al. |
| 7,146,210 B2 | 12/2006 | Palti |
| 7,147,638 B2 | 12/2006 | Chapman et al. |
| 7,151,964 B2 | 12/2006 | Desai et al. |
| 7,153,300 B2 | 12/2006 | Goble |
| 7,156,842 B2 | 1/2007 | Sartor et al. |
| 7,156,844 B2 | 1/2007 | Reschke et al. |
| 7,156,846 B2 | 1/2007 | Dycus et al. |
| 7,160,293 B2 | 1/2007 | Sturm et al. |
| 7,163,536 B2 | 1/2007 | Godara |
| 7,166,986 B2 | 1/2007 | Kendall |

| Patent | Date | Inventor |
|---|---|---|
| 7,169,144 B2 | 1/2007 | Hoey et al. |
| 7,172,591 B2 | 2/2007 | Harano et al. |
| 7,175,618 B2 | 2/2007 | Dabney et al. |
| 7,175,621 B2 | 2/2007 | Heim et al. |
| 7,192,427 B2 | 3/2007 | Chapelon et al. |
| 7,194,297 B2 | 3/2007 | Talpade et al. |
| 7,195,627 B2 | 3/2007 | Amoah et al. |
| 7,197,363 B2 | 3/2007 | Prakash et al. |
| 7,200,010 B2 | 4/2007 | Broman et al. |
| 7,200,445 B1 | 4/2007 | Dalbee et al. |
| 7,203,556 B2 | 4/2007 | Daners |
| 7,211,081 B2 | 5/2007 | Goble |
| 7,214,224 B2 | 5/2007 | Goble |
| 7,217,269 B2 | 5/2007 | El-Galley et al. |
| 7,220,260 B2 | 5/2007 | Fleming et al. |
| 7,223,264 B2 | 5/2007 | Daniel et al. |
| 7,226,447 B2 | 6/2007 | Uchida et al. |
| 7,229,469 B1 | 6/2007 | Witzel et al. |
| 7,232,437 B2 | 6/2007 | Berman et al. |
| 7,233,278 B2 | 6/2007 | Eriksson |
| 7,238,181 B2 | 7/2007 | Daners et al. |
| 7,238,183 B2 | 7/2007 | Kreindel |
| 7,244,255 B2 | 7/2007 | Daners et al. |
| 7,247,155 B2 | 7/2007 | Hoey et al. |
| 7,250,048 B2 | 7/2007 | Francischelli et al. |
| 7,250,746 B2 | 7/2007 | Oswald et al. |
| 7,255,694 B2 | 8/2007 | Keppel |
| 7,258,688 B1 | 8/2007 | Shah et al. |
| 7,282,048 B2 | 10/2007 | Goble et al. |
| 7,282,049 B2 | 10/2007 | Orszulak et al. |
| 7,285,117 B2 | 10/2007 | Krueger et al. |
| 7,294,127 B2 | 11/2007 | Leung et al. |
| 7,300,435 B2 | 11/2007 | Wham et al. |
| 7,300,437 B2 | 11/2007 | Pozzato |
| 7,303,557 B2 | 12/2007 | Wham et al. |
| 7,305,311 B2 | 12/2007 | Van Zyl |
| 7,317,954 B2 | 1/2008 | McGreevy |
| 7,317,955 B2 | 1/2008 | McGreevy |
| 7,324,357 B2 | 1/2008 | Miura et al. |
| 7,333,859 B2 | 2/2008 | Rinaldi et al. |
| 7,341,586 B2 | 3/2008 | Daniel et al. |
| 7,344,532 B2 | 3/2008 | Goble et al. |
| 7,353,068 B2 | 4/2008 | Tanaka et al. |
| 7,354,436 B2 | 4/2008 | Rioux et al. |
| 7,357,800 B2 | 4/2008 | Swanson |
| 7,364,577 B2 | 4/2008 | Wham et al. |
| 7,364,578 B2 | 4/2008 | Francischelli et al. |
| 7,364,972 B2 | 4/2008 | Ono et al. |
| 7,367,972 B2 | 5/2008 | Francischelli et al. |
| RE40,388 E | 6/2008 | Gines |
| 7,396,336 B2 | 7/2008 | Orszulak et al. |
| 7,402,754 B2 | 7/2008 | Kirwan, Jr. et al. |
| 574,323 A1 | 8/2008 | Waaler |
| 7,407,502 B2 | 8/2008 | Strul et al. |
| 7,416,437 B2 | 8/2008 | Sartor et al. |
| 7,416,549 B2 | 8/2008 | Young et al. |
| 7,422,582 B2 | 9/2008 | Malackowski et al. |
| 7,422,586 B2 | 9/2008 | Morris et al. |
| 7,425,835 B2 | 9/2008 | Eisele |
| 7,465,302 B2 | 12/2008 | Odell et al. |
| 7,470,272 B2 | 12/2008 | Mulier et al. |
| 7,477,080 B1 | 1/2009 | Fest |
| 7,479,140 B2 | 1/2009 | Ellman et al. |
| 7,491,199 B2 | 2/2009 | Goble |
| 7,491,201 B2 | 2/2009 | Shields et al. |
| 7,503,917 B2 | 3/2009 | Sartor et al. |
| 7,513,896 B2 | 4/2009 | Orszulak |
| 7,517,351 B2 | 4/2009 | Culp et al. |
| 7,525,398 B2 | 4/2009 | Nishimura et al. |
| 7,582,084 B2 | 9/2009 | Swanson et al. |
| 7,628,786 B2 | 12/2009 | Plaven et al. |
| 7,648,499 B2 | 1/2010 | Orszulak et al. |
| 7,651,492 B2 | 1/2010 | Wham |
| 7,651,493 B2 | 1/2010 | Arts et al. |
| 2001/0008966 A1 | 7/2001 | Arndt et al. |
| 2001/0016762 A1 | 8/2001 | Carr |
| 2001/0020178 A1 | 9/2001 | Arndt et al. |
| 2002/0000234 A1 | 1/2002 | Manker et al. |
| 2002/0029036 A1 | 3/2002 | Goble et al. |
| 2002/0165529 A1 | 11/2002 | Danek |
| 2002/0193849 A1 | 12/2002 | Fenn et al. |
| 2003/0014043 A1 | 1/2003 | Henry et al. |
| 2003/0023238 A1 | 1/2003 | Manker et al. |
| 2003/0055471 A1 | 3/2003 | Fenn et al. |
| 2003/0065317 A1 | 4/2003 | Rudie et al. |
| 2003/0069619 A1 | 4/2003 | Fenn et al. |
| 2003/0144655 A1 | 7/2003 | Panescu |
| 2003/0181898 A1 | 9/2003 | Bowers |
| 2003/0191513 A1 | 10/2003 | Manker et al. |
| 2003/0199863 A1 | 10/2003 | Swanson et al. |
| 2004/0015159 A1 | 1/2004 | Slater et al. |
| 2004/0030330 A1 | 2/2004 | Brassell et al. |
| 2004/0032301 A1 | 2/2004 | Schultheiss et al. |
| 2004/0049254 A1 | 3/2004 | Longo |
| 2004/0068304 A1 | 4/2004 | Paton |
| 2004/0097912 A1 | 5/2004 | Gonnering |
| 2004/0122420 A1 | 6/2004 | Amoah |
| 2004/0133254 A1 | 7/2004 | Sterzer et al. |
| 2004/0143263 A1 | 7/2004 | Schechter et al. |
| 2004/0172016 A1 | 9/2004 | Bek et al. |
| 2004/0193147 A1 | 9/2004 | Malecki et al. |
| 2004/0215179 A1 | 10/2004 | Swoyer et al. |
| 2004/0215182 A1 | 10/2004 | Lee |
| 2004/0243120 A1 | 12/2004 | Orszulak et al. |
| 2004/0243200 A1 | 12/2004 | Turner et al. |
| 2005/0004564 A1 | 1/2005 | Wham |
| 2005/0004634 A1 | 1/2005 | Ricart et al. |
| 2005/0021020 A1 | 1/2005 | Blaha et al. |
| 2005/0038419 A9 | 2/2005 | Arnold et al. |
| 2005/0109111 A1 | 5/2005 | Manlove et al. |
| 2005/0137662 A1 | 6/2005 | Morris et al. |
| 2005/0143795 A1 | 6/2005 | Habib et al. |
| 2005/0149010 A1 | 7/2005 | Turovskiy et al. |
| 2005/0149012 A1 | 7/2005 | Penny et al. |
| 2005/0182393 A1 | 8/2005 | Abboud et al. |
| 2005/0182398 A1 | 8/2005 | Paterson |
| 2005/0197659 A1 | 9/2005 | Bahney |
| 2005/0203504 A1 | 9/2005 | Wham et al. |
| 2005/0228370 A1 | 10/2005 | Sterzer et al. |
| 2005/0240239 A1 | 10/2005 | Boveja et al. |
| 2005/0245920 A1 | 11/2005 | Vitullo et al. |
| 2006/0004351 A1 | 1/2006 | Arless et al. |
| 2006/0015095 A1 | 1/2006 | Desinger et al. |
| 2006/0015161 A1 | 1/2006 | Longo et al. |
| 2006/0015162 A1 | 1/2006 | Edward et al. |
| 2006/0025760 A1 | 2/2006 | Podhajsky |
| 2006/0030914 A1 | 2/2006 | Eggers et al. |
| 2006/0079774 A1 | 4/2006 | Anderson |
| 2006/0079871 A1 | 4/2006 | Plaven et al. |
| 2006/0106375 A1 | 5/2006 | Werneth et al. |
| 2006/0111711 A1 | 5/2006 | Goble |
| 2006/0116673 A1 | 6/2006 | Gauthier et al. |
| 2006/0142753 A1 | 6/2006 | Francischelli et al. |
| 2006/0161148 A1 | 7/2006 | Behnke |
| 2006/0178664 A1 | 8/2006 | Keppel |
| 2006/0224152 A1 | 10/2006 | Behnke et al. |
| 2006/0291178 A1 | 12/2006 | Shih |
| 2006/0293649 A1 | 12/2006 | Lorang et al. |
| 2007/0038209 A1 | 2/2007 | Buysse et al. |
| 2007/0088413 A1 | 4/2007 | Weber et al. |
| 2007/0093800 A1 | 4/2007 | Wham et al. |
| 2007/0093801 A1 | 4/2007 | Behnke |
| 2007/0135812 A1 | 6/2007 | Sartor |
| 2007/0173802 A1 | 7/2007 | Keppel |
| 2007/0173803 A1 | 7/2007 | Wham et al. |
| 2007/0173804 A1 | 7/2007 | Wham et al. |
| 2007/0173805 A1 | 7/2007 | Weinberg et al. |
| 2007/0173806 A1 | 7/2007 | Orszulak et al. |
| 2007/0173810 A1 | 7/2007 | Orszulak |
| 2007/0173813 A1 | 7/2007 | Odom |
| 2007/0203481 A1 | 8/2007 | Gregg et al. |
| 2007/0208339 A1 | 9/2007 | Arts et al. |
| 2007/0225698 A1 | 9/2007 | Orszulak et al. |
| 2007/0250052 A1 | 10/2007 | Wham |
| 2007/0265612 A1 | 11/2007 | Behnke et al. |
| 2007/0282320 A1 | 12/2007 | Buysse et al. |
| 2007/0293858 A1 | 12/2007 | Fischer |
| 2008/0015563 A1 | 1/2008 | Hoey et al. |

| | | | | | | |
|---|---|---|---|---|---|---|
| 2008/0015564 A1 | 1/2008 | Wham et al. | EP | 310431 | 4/1989 | |
| 2008/0039831 A1 | 2/2008 | Odom et al. | EP | 325456 | 7/1989 | |
| 2008/0039836 A1 | 2/2008 | Odom et al. | EP | 336742 | 10/1989 | |
| 2008/0082094 A1 | 4/2008 | McPherson et al. | EP | 390937 | 10/1990 | |
| 2008/0082095 A1 | 4/2008 | Shores et al. | EP | 556705 | 8/1993 | |
| 2008/0082096 A1 | 4/2008 | Shores et al. | EP | 569130 | 11/1993 | |
| 2008/0125767 A1 | 5/2008 | Blaha | EP | 608609 | 8/1994 | |
| 2008/0177199 A1 | 7/2008 | Podhajsky | EP | 694291 | 1/1996 | |
| 2008/0248685 A1 | 10/2008 | Sartor et al. | EP | 836868 | 4/1998 | |
| 2008/0281315 A1 | 11/2008 | Gines | EP | 878169 | 11/1998 | |
| 2008/0281316 A1 | 11/2008 | Carlton et al. | EP | 882955 | 12/1998 | |
| 2008/0287791 A1 | 11/2008 | Orszulak et al. | EP | 1051948 | 11/2000 | |
| 2008/0287838 A1 | 11/2008 | Orszulak et al. | EP | 1053720 | 11/2000 | |
| 2009/0018536 A1 | 1/2009 | Behnke | EP | 1151725 | 11/2001 | |
| 2009/0024120 A1 | 1/2009 | Sartor | EP | 1278007 | 1/2003 | |
| 2009/0036883 A1 | 2/2009 | Behnke | EP | 1293171 | 3/2003 | |
| 2009/0069801 A1 | 3/2009 | Jensen et al. | EP | 1472984 | 11/2004 | |
| 2009/0082765 A1 | 3/2009 | Collins et al. | EP | 1495712 | 1/2005 | |
| 2009/0157071 A1 | 6/2009 | Wham et al. | EP | 1500378 | 1/2005 | |
| 2009/0157072 A1 | 6/2009 | Wham et al. | EP | 1535581 | 6/2005 | |
| 2009/0157073 A1 | 6/2009 | Orszulak | EP | 1609430 | 12/2005 | |
| 2009/0157075 A1 | 6/2009 | Wham et al. | EP | 1366724 | 1/2006 | |
| 2009/0234350 A1 | 9/2009 | Behnke et al. | EP | 1707144 | 3/2006 | |
| 2009/0237169 A1 | 9/2009 | Orszulak | EP | 1645235 | 4/2006 | |
| 2009/0248003 A1 | 10/2009 | Orszulak | EP | 880220 | 6/2006 | |
| 2009/0248006 A1 | 10/2009 | Paulus et al. | EP | 1681026 | 7/2006 | |
| 2009/0254077 A1 | 10/2009 | Craig | EP | 1707143 | 10/2006 | |
| 2009/0259224 A1 | 10/2009 | Wham et al. | EP | 1707144 | 10/2006 | |
| 2009/0292283 A1 | 11/2009 | Odom | EP | 1744354 | 1/2007 | |
| 2009/0306648 A1 | 12/2009 | Podhajsky et al. | EP | 1776929 | 4/2007 | |
| 2010/0030210 A1 | 2/2010 | Paulus | EP | 1810628 | 7/2007 | |
| 2010/0042093 A9 | 2/2010 | Wham et al. | EP | 1810630 | 7/2007 | |
| 2010/0057076 A1 | 3/2010 | Behnke et al. | EP | 1810633 | 7/2007 | |
| 2010/0063494 A1 | 3/2010 | Orszulak | EP | 1854423 | 11/2007 | |
| 2010/0063497 A1 | 3/2010 | Orszulak | EP | 1862137 | 12/2007 | |
| 2010/0068949 A1 | 3/2010 | Plaven et al. | FR | 1275415 | 10/1961 | |
| 2010/0079215 A1 | 4/2010 | Brannan et al. | FR | 1347865 | 11/1963 | |
| 2010/0082022 A1 | 4/2010 | Haley et al. | FR | 2313708 | 12/1976 | |
| 2010/0082023 A1 | 4/2010 | Brannan et al. | FR | 2364461 | 7/1978 | |
| 2010/0082024 A1 | 4/2010 | Brannan et al. | FR | 2502935 | 10/1982 | |
| 2010/0082025 A1 | 4/2010 | Brannan et al. | FR | 2517953 | 6/1983 | |
| 2010/0082083 A1 | 4/2010 | Brannan et al. | FR | 2573301 | 5/1986 | |
| 2010/0082084 A1 | 4/2010 | Brannan et al. | GB | 607850 | 9/1948 | |
| 2010/0094271 A1 | 4/2010 | Ward et al. | GB | 702510 | 1/1954 | |
| 2010/0094275 A1 | 4/2010 | Wham | GB | 855459 | 11/1960 | |
| 2010/0094285 A1 | 4/2010 | Arts et al. | GB | 902775 | 8/1962 | |
| 2010/0094288 A1 | 4/2010 | Kerr | GB | 2154881 | 9/1985 | |
| | | | GB | 2164473 | 3/1986 | |
| FOREIGN PATENT DOCUMENTS | | | GB | 2214430 | 9/1989 | |
| DE | 1099658 | 2/1961 | GB | 2331247 | 5/1999 | |
| DE | 1139927 | 11/1962 | GB | 2358934 | 8/2001 | |
| DE | 1149832 | 6/1963 | GB | 2434872 | 8/2007 | |
| DE | 1439302 | 1/1969 | SU | 166452 | 1/1965 | |
| DE | 2439587 | 2/1975 | SU | 727201 | 4/1980 | |
| DE | 2455174 | 5/1975 | WO | WO92/06642 | 4/1992 | |
| DE | 2407559 | 8/1975 | WO | WO92/07622 | 5/1992 | |
| DE | 2602517 | 7/1976 | WO | WO93/24066 | 12/1993 | |
| DE | 2504280 | 8/1976 | WO | WO94/10922 | 5/1994 | |
| DE | 2540968 | 3/1977 | WO | WO94/24949 | 11/1994 | |
| DE | 2820908 | 11/1978 | WO | WO94/28809 | 12/1994 | |
| DE | 2803275 | 8/1979 | WO | WO95/09577 | 4/1995 | |
| DE | 2823291 | 11/1979 | WO | WO95/19148 | 7/1995 | |
| DE | 2946728 | 5/1981 | WO | WO95/25471 | 9/1995 | |
| DE | 3143421 | 5/1982 | WO | WO95/25472 | 9/1995 | |
| DE | 3045996 | 7/1982 | WO | WO96/02180 | 2/1996 | |
| DE | 3120102 | 12/1982 | WO | WO96/04860 | 2/1996 | |
| DE | 3510586 | 10/1986 | WO | WO96/08794 | 3/1996 | |
| DE | 3604823 | 8/1987 | WO | WO96/18349 | 6/1996 | |
| DE | 390937 | 4/1989 | WO | WO96/29946 | 10/1996 | |
| DE | 3904558 | 8/1990 | WO | WO96/39086 | 12/1996 | |
| DE | 3942998 | 7/1991 | WO | WO96/39088 | 12/1996 | |
| DE | 4206433 | 9/1993 | WO | WO96/39914 | 12/1996 | |
| DE | 4339049 | 5/1995 | WO | WO97/06739 | 2/1997 | |
| DE | 19506363 | 8/1996 | WO | WO97/06740 | 2/1997 | |
| DE | 19717411 | 11/1998 | WO | WO97/06855 | 2/1997 | |
| DE | 19848540 | 5/2000 | WO | WO97/11648 | 4/1997 | |
| EP | 246350 | 11/1987 | WO | WO97/17029 | 5/1997 | |
| EP | 267403 | 5/1988 | WO | WO98/07378 | 2/1998 | |
| EP | 296777 | 12/1988 | WO | WO98/18395 | 5/1998 | |

| | | |
|---|---|---|
| WO | WO98/27880 | 7/1998 |
| WO | WO99/12607 | 3/1999 |
| WO | WO99/56647 | 11/1999 |
| WO | WO00/54683 | 9/2000 |
| WO | WO01/01847 | 1/2001 |
| WO | WO02/00129 | 1/2002 |
| WO | WO02/11634 | 2/2002 |
| WO | 02/32333 | 4/2002 |
| WO | WO02/45589 | 6/2002 |
| WO | WO02/47565 | 6/2002 |
| WO | WO02/053048 | 7/2002 |
| WO | WO02/088128 | 7/2002 |
| WO | WO03/090630 | 11/2003 |
| WO | WO03/090635 | 11/2003 |
| WO | WO03/092520 | 11/2003 |
| WO | WO2004/028385 | 4/2004 |
| WO | WO2004/098385 | 4/2004 |
| WO | WO2004/043240 | 5/2004 |
| WO | WO2004/047659 | 6/2004 |
| WO | WO2004/052182 | 6/2004 |
| WO | WO2004/103156 | 12/2004 |
| WO | WO2005/046496 | 5/2005 |
| WO | WO2005/048809 | 6/2005 |
| WO | WO2005/050151 | 6/2005 |
| WO | WO2005/060365 | 7/2005 |
| WO | WO2005/060849 | 7/2005 |
| WO | WO2006/050888 | 5/2006 |
| WO | WO2006/105121 | 10/2006 |
| WO | WO2007/055491 | 5/2007 |
| WO | WO2007/105963 | 9/2007 |
| WO | WO2008/044013 | 4/2008 |
| WO | WO2008/070562 | 6/2008 |
| WO | WO2008/071914 | 6/2008 |
| WO | WO2008/110756 | 9/2008 |

OTHER PUBLICATIONS

Japanese Office Action for Application No. 2006-514179 dated Nov. 30, 2010.
US 6,878,148, Apr. 2005, Goble et al. (withdrawn).
U.S. Appl. No. 10/406,690, filed Apr. 3, 2003.
U.S. Appl. No. 10/573,713, filed Mar. 28, 2006.
U.S. Appl. No. 10/761,524, filed Jan. 21, 2004.
U.S. Appl. No. 11/242,458, filed Oct. 3, 2005.
U.S. Appl. No. 12/351,935, filed Jan. 12, 2009.
U.S. Appl. No. 12/351,947, filed Jan. 12, 2009.
U.S. Appl. No. 12/351,960, filed Jan. 12, 2009.
U.S. Appl. No. 12/351,970, filed Jan. 12, 2009.
U.S. Appl. No. 12/351,980, filed Jan. 12, 2009.
U.S. Appl. No. 12/353,002, filed Jan. 13, 2009.
U.S. Appl. No. 12/353,012, filed Jan. 13, 2009.
U.S. Appl. No. 12/477,245, filed Jun. 3, 2009.
U.S. Appl. No. 12/534,308, filed Aug. 3, 2009.
U.S. Appl. No. 12/540,190, filed Aug. 12, 2009.
U.S. Appl. No. 12/549,563, filed Aug. 28, 2009.
U.S. Appl. No. 12/556,770, filed Sep. 10, 2009.
U.S. Appl. No. 12/566,173, filed Sep. 24, 2009.
U.S. Appl. No. 12/566,233, filed Sep. 24, 2009.
U.S. Appl. No. 12/567,966, filed Sep. 28, 2009.
U.S. Appl. No. 12/613,876, filed Nov. 6, 2009.
U.S. Appl. No. 12/619,234, filed Nov. 16, 2009.
U.S. Appl. No. 12/639,210, filed Dec. 16, 2009.
U.S. Appl. No. 12/665,081, filed Dec. 17, 2009.
U.S. Appl. No. 12/712,712, filed Feb. 25, 2010.
U.S. Appl. No. 12/713,956, filed Feb. 26, 2010.
U.S. Appl. No. 12/715,212, filed Mar. 1, 2010.
U.S. Appl. No. 12/754,420, filed Apr. 5, 2010.
U.S. Appl. No. 12/754,429, filed Apr. 5, 2010.
U.S. Appl. No. 12/772,345, filed May 3, 2010.
Wald et al., "Accidental Burns", JAMA, Aug. 16, 1971, vol. 217, No. 7, pp. 916-921.
Vallfors et al., "Automatically Controlled Bipolar Electrosoagulation—'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" in William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.

International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.
International Search Report EP09005160.8 dated Aug. 27, 2009.
International Search Report EP09009860 dated Dec. 8, 2009.
International Search Report EP09012386 dated Apr. 1, 2010.
International Search Report EP09012392 dated Mar. 30, 2010.
International Search Report EP09012396 dated Apr. 7, 2010.
International Search Report EP09012400 dated Apr. 7, 2010.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP10150564.2 dated Mar. 29, 2010.
International Search Report EP10150565.9 dated Mar. 12, 2010.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.

* cited by examiner

METHOD AND SYSTEM FOR PROGRAMMING AND CONTROLLING AN ELECTROSURGICAL GENERATOR SYSTEM

PRIORITY

This application is a divisional of application Ser. No. 10/554,837 filed Dec. 19, 2006 which claims priority to an application entitled "METHOD AND SYSTEM FOR PROGRAMMING AND CONTROLLING AN ELECTROSURGICAL GENERATOR SYSTEM" filed in the United States Patent and Trademark Office on May 1, 2003 and assigned Ser. No. 60/466,954, the contents of which are hereby incorporated by reference.

BACKGROUND

1. Technical Field

The present disclosure is directed to electrosurgery and, in particular, to a method and system for programming and controlling an electrosurgical generator system.

2. Description of the Related Art

Electrosurgery entails the use of electrosurgical energy to cut or coagulate tissue, or perform some other type of surgical procedure. An electrosurgical generator system is used for generating the electrosurgical energy and delivering the same to an electrode connected to the generator. The electrode is then brought into contact with tissue and depending on the frequency and other parameters of the electrosurgical energy, the tissue is either cut, coagulated, sealed, etc.

In order to achieve desired surgical results when operating the electrosurgical generator system in one of several control modes, e.g., cut, coagulate and blend, the electrosurgical generator system needs to be programmed to generate electrosurgical energy having output parameters with predetermined values. These desired output parameters typically include the frequency, power (amplitude), duty cycle, and waveform-type of the electrosurgical energy, as well as the output current and output voltage of the electrosurgical generator system.

It is evident that by programming the electrosurgical generator system, one can control various parameters, including other factors, such as the maximum allowable temperature of the tissue during electrosurgery, rate of change of impedance, etc., prior to initiating the electrosurgical procedure.

Accordingly, the present disclosure provides a method and system capable of enabling an individual to quickly create new electrosurgical applications without major re-programming of the software system of an electrosurgical generator system.

SUMMARY

A method and system are disclosed capable of enabling an individual to quickly create new electrosurgical applications without major re-programming of the software system of an electrosurgical generator system. In one embodiment, a programmable electrosurgical generator system has an RF output stage for outputting at least one RF operating waveform for performing an electrosurgical procedure. The programmable electrosurgical generator system includes an inner loop system to change at least one parameter of the at least one RF operating waveform; an outer loop system to provide at least one operating command to the inner loop system; and a configuration control system that modifies at least one of the inner and outer loop systems based on received data from a sensor module.

A control loop system is chiefly responsible for the operation of the electrosurgical generator system and it is composed of three basic components: an inner loop system which is responsible for changing and sculpting basic RF output; an outer loop system which is responsible for setting the output target of the inner loop based on a variety of algorithms such as the control of temperature; and a configuration control system which is responsible for reprogramming the inner and outer loop systems "on-the-fly" or in virtual real-time for the inner and outer loop systems to change operation.

All user programming is preferably accomplished using at least one input device, such as a keyboard, touch-screen display, etc., while the software programming may be based on a file-based programming language to input programming commands to the electrosurgical generator system. The combination of the two inputted programming commands are stored into command files and define all aspects and parameters of the electrosurgical generator system.

The simple input and storage of the programming commands according to the present disclosure allows for easy creation and modification of new electrosurgical generator modes. For example, a mode can be created by inputting programming commands and storing the same in a command file, subsequent modes can easily be created by modifying associated parameters and storing them as a new command file.

Further features of the above embodiments will become more readily apparent to those skilled in the art from the following detailed description when taken in conjunction with the drawings.

BRIEF DESCRIPTION OF THE DRAWINGS

Various embodiments will be described herein below with reference to the drawings wherein.

DETAILED DESCRIPTION

Figure 1:
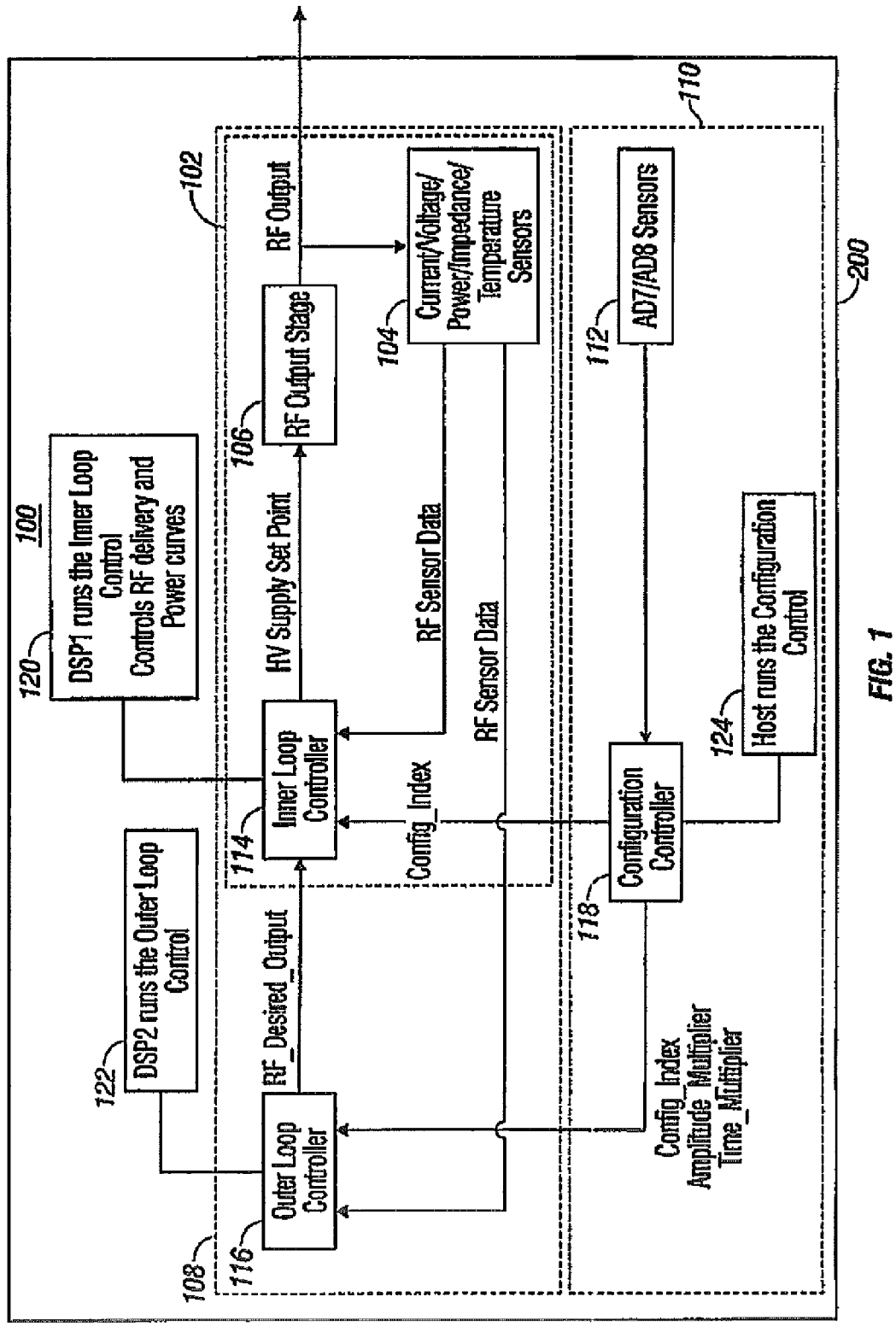
FIG. 1 is a block diagram of a control loop system of an electrosurgical generator system in accordance with the present disclosure.

Reference should be made to the drawings where like reference numerals refer to similar elements. Referring to FIG. 1, there is shown a block diagram of an embodiment of a control loop system for an electrosurgical generator system in accordance with the present disclosure. The control loop system is designated generally by reference numeral 100 and it is designed to enable a software developer to efficiently program and control the operation of the electrosurgical generator system 200. The electrosurgical generator system 200 is particularly designed for the easy creation of multiple different electrosurgical systems. The method and system of the present disclosure enables an individual to efficiently create new application modes by creating configuration or command files for downloading or programming these new modes into the electrosurgical generator system for creating new surgical applications without changing the underlying software system.

The control loop system 100 is chiefly responsible for the operation of the electrosurgical generator system 200 and it is composed of three basic components: an inner loop system 102 which is responsible for changing and sculpting basic RF output (e.g., current, power, or voltage output, duty cycle, frequency), and inner loop control system dynamics of an RF output stage 106 based on user and/or sensor inputs from various sensors 104 and/or user input devices (not shown); an outer loop system 108 which is responsible for controlling the inner loop setpoint based on a variety of algorithms (e.g., temperature control, impedance control, pulse control, vessel sealing, etc.) based on user and/or sensor inputs from the various sensors 104 and time and/or user input devices (not shown); and a configuration control system 110 which is responsible for changing the programming of the inner and outer loop systems 102, 108 "on-the-fly" or in virtual real-time based on user or sensor inputs received from various sensors 112 and/or user input devices (not shown).

Figure 2A:
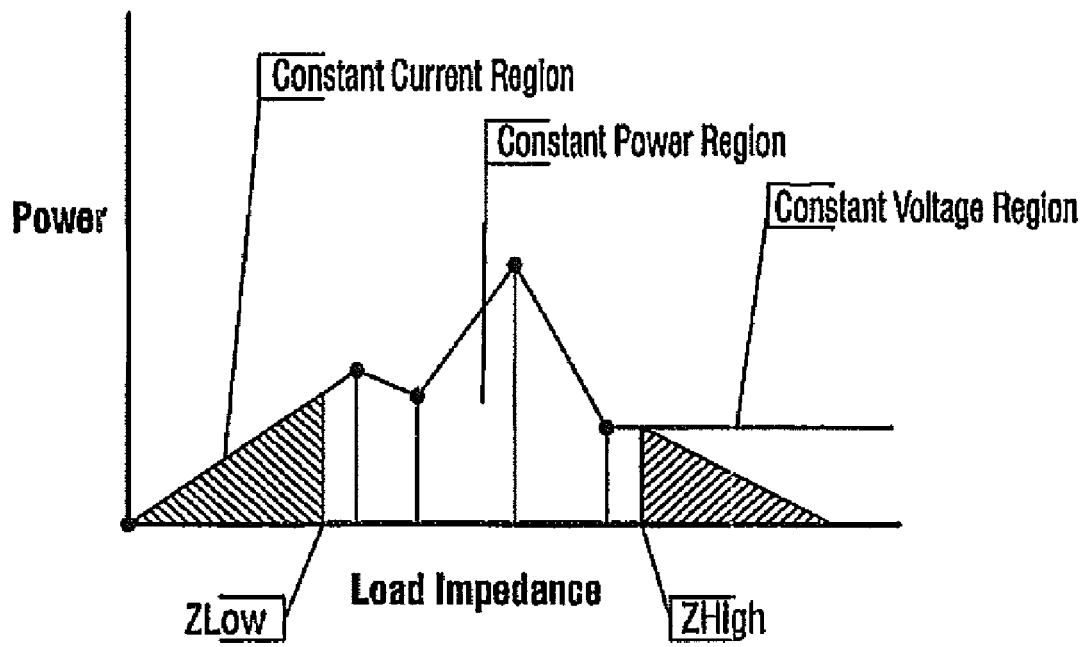
FIGS. 2A-D illustrate charts showing output waveforms indicative of various output parameters of the electrosurgical generator system in accordance with the present disclosure.

FIGS. 2A-2D illustrate charts showing the RF output indicative of various inner loop output parameters of the electrosurgical generator system 200. FIG. 2A is a chart plotting the output power versus the load impedance where the output power is sculpted, e.g., the output power is not constant over a load impedance range. The electrosurgical generator system 200 is able to control the inner loop system 102 to sculpt the output power based on user and/or sensor inputs received from various sensors 104, 112 and/or user input devices.

Figure 2B:
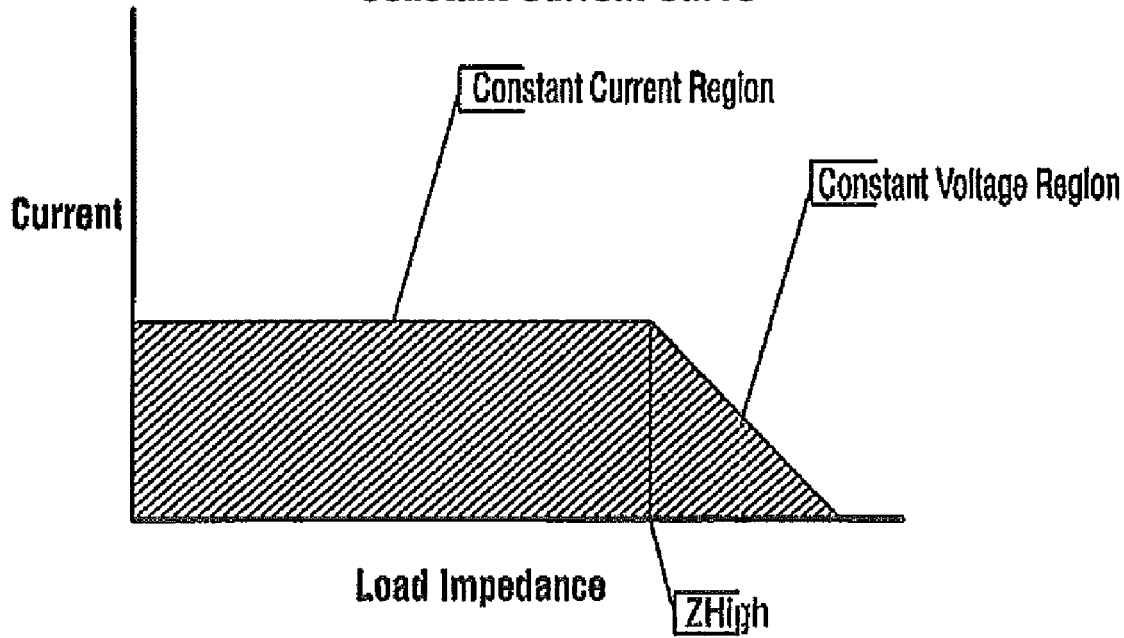
Figure 2C:
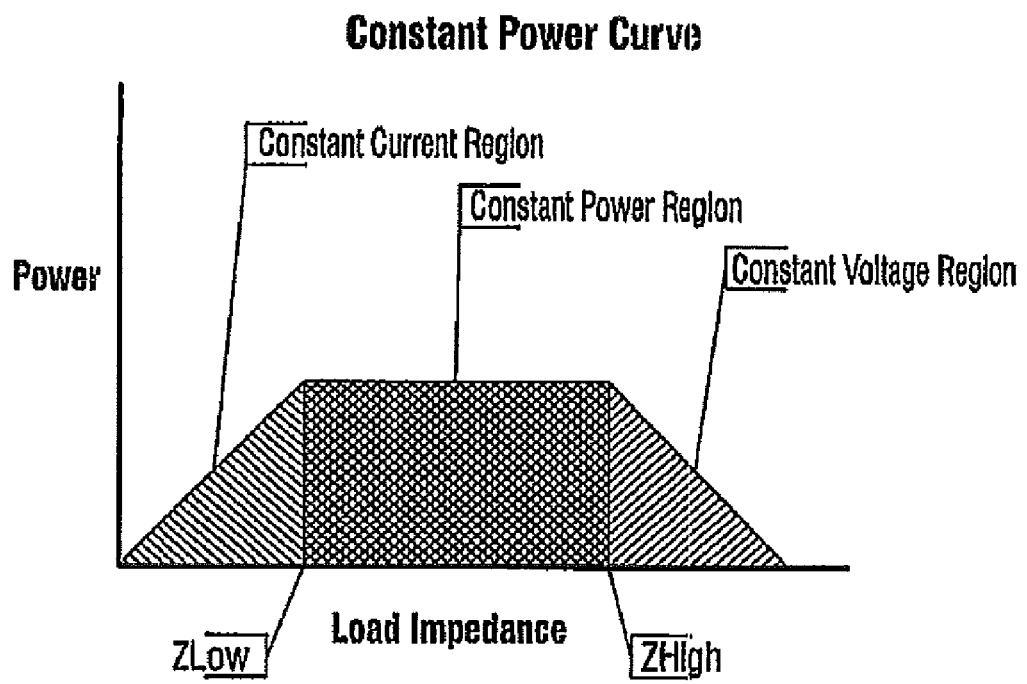
Figure 2D:
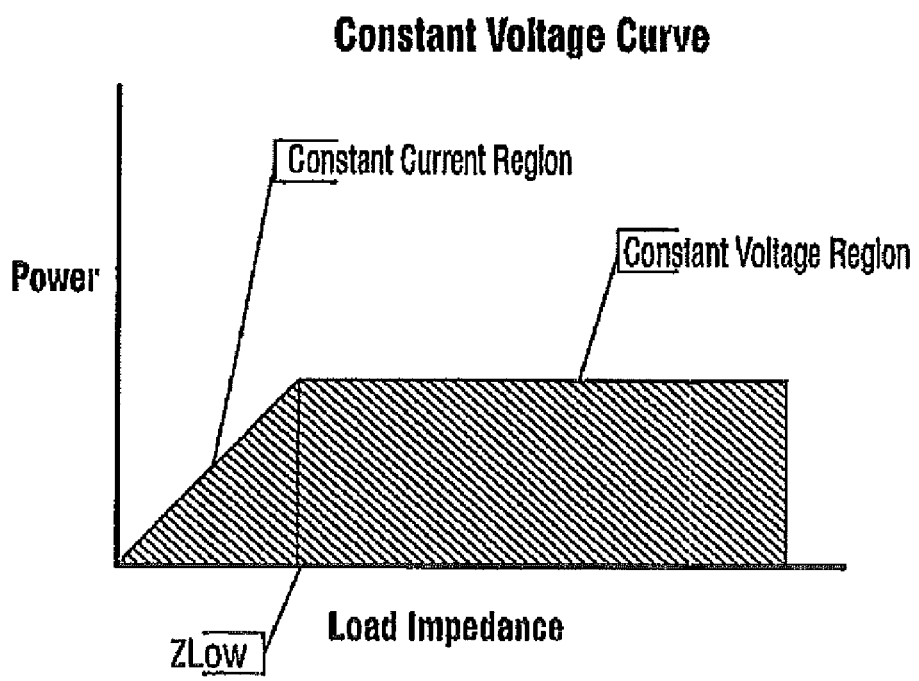

With reference to FIGS. 2B-2D, the electrosurgical generator system 200 is also able to maintain the output constant. FIG. 2B shows the output current being maintained at a constant level over a load impedance range. FIG. 2C shows the output power being maintained at a constant level over a load impedance range. FIG. 2D shows the output voltage being maintained at a constant level over a load impedance range.

As shown by FIG. 1, the inner loop system 102 is controlled by an inner loop controller 114, the outer loop system 108 is controlled by an outer loop controller 116, and the configuration control system 110 is controlled by a configuration controller 118. The controllers 114, 116 perform their various functions by the execution of a set of programmable instructions by at least one microprocessor and/or at least one digital signal processor (DSP), e.g., DSPs 120, 122, respectively.

The configuration controller 118 performs its various functions by the execution of a set of programmable instructions executed by at least one microprocessor and/or a DSP, e.g., DSP 124. The controllers 114, 116, 118 are configured for receiving inputted programming commands for operating the electrosurgical generator system 200.

All programming is preferably accomplished using at least one input device, such as a keyboard, touch-screen display, remote computer system, etc., to input the programming commands to the electrosurgical generator system 200. The inputted programming commands are stored into command files within at least one memory module, such as a RAM module, and define all aspects and parameters of the electrosurgical generator system 200.

The simple input or download and storage of the programming commands according to the present disclosure allows for easy creation and modification of new electrosurgical generator modes. For example, one mode can be created by inputting programming commands and storing the same in a command file. A new mode can be created based on the original programming.

A description will now be presented with reference to programming the at least one microprocessor by way of a programming language in a preferred embodiment for controlling and programming the electrosurgical generator system 200 of the present disclosure.

I. Configuration Control System

The set of programmable instructions for operating the electrosurgical generator system 200 in accordance with the present disclosure has been designed to enable two analog inputs to the configuration controller 118 to control the mode (outer and inner loop programming) and the desired output (current (I), power (P), voltage (V), etc. depending on the control mode selected) of the electrosurgical generator system 200.

In an exemplary embodiment of the present disclosure, the method of mode control is accomplished by making a data structure, e.g., Local_Cfg[ ], an array. When a mode switch is desired, a host variable, e.g., Config_index, is adjusted and then copied to a processing file, e.g., Out_Local_IO.Config_index, where it switches an active command file, e.g., Local_Cfg[Local_IO.Config_Index].

The method of desired output programming is accomplished by adjusting a host variable, e.g., Out_Local_IO.Desired_Amplitude_Multiplier, where Desired_Amplitude_Multiplier represents a multiplier value for adjusting the output curves of the outer loop system 108 when enabled or is passed directly to the inner loop system 102 as a current/power/voltage level if the outer loop system 108 is disabled.

I.a. Configuration Selection Control

The configuration selection is programmed by filling the variable, e.g., Local_Cfg[ ], with the data from the sets of command files. The configuration index is first specified, then the data is read from the command files, then the next index is specified, etc.

I.a.1. Command File Programming

The programming of the configuration control system 110 is controlled by a Meta command file. This command file loads the Local_Cfg[ ] array with each configuration and specifies how the configuration and Desired_Amplitude_Multiplier is controlled.

To specify which location in the Local_Cfg[ ] array is to be filled, the following command is used:

CONFIG_INDEX x, where x specifies the location to be filled (0-7).

To specify which configuration is to be loaded in the memory module, the following command is used:

INCLUDE_FILE xxx, where xxx is a valid path and filename of outer and inner loop command files which define the configuration to be loaded in the memory module.

An example is provided below:

```
// Load Config Index Location 0
#CONFIG_INDEX      0
// Inner Loop definition
#INCLUDE_FILE
C:\LRT_TRT\Code\Cmd_Files\CP_472k_Inner_Loop.cmd
// Load Outer Loop definition
#INCLUDE_FILE
C:\LRT_TRT\Code\Cmd_Files\Temp_Outer_Loop.cmd
// Load Config Index location 1
#CONFIG_INDEX      1
// Inner Loop definition
#INCLUDE_FILE
C:\LRT_TRT\Code\Cmd_Files\CP_250k_Inner_Loop.cmd
// Load Outer Loop definition
#INCLUDE_FILE
C:\LRT_TRT\Code\Cmd_Files\DZ_Outer_Loop.cmd
```

I.b. Mode Selection Control

Mode selection can be programmed to be selected by one of three inputs: a user input device (e.g., a keyboard), AD7 or AD8, where AD7 and AD8 are sensor modules. Mode modification can be programmed to be controlled by one of three inputs: a user input device (e.g., a keyboard), AD7 or AD8. The operation of the mode selection and mode modification control is that one control input can be set to select the mode, then another control can make the fine adjustments to that selection. The mode modification may be done in an additive fashion as shown in the example below:

Actual Mode=Mode(AD7)+Modifier(AD8).

I.b.1. Command File Programming

A Mode Selection Algorithm which controls how the active mode switching is set may be selected.

The valid exemplary selection choices are the following:

MODE_SEL_ALG_IS_KEYBOARD -keyboard sets the active mode.
MODE_SEL_ALG_IS_AD7
MODE_SEL_ALG_IS_AD8

A Mode Modification Algorithm which controls how the active mode switching is set by a modifier also may be selected.

The valid exemplary selection choices are the following:

MODE_MODIFIER_SEL IS OFF -No modifier is used on active mode switching.
MODE_MODIFIER_SEL_IS_AD7
MODE_MODIFIER_SEL_IS_AD8

I.e. Amplitude Selection Control

Amplitude multiplication selection can be selected by one of three inputs: a user input device (e.g., a keyboard), AD7 or AD8. Amplitude multiplication modification can be controlled by one of three inputs: keyboard, AD7 or AD8. The operation of the selection and modification control is that one control input can be set to select the amplitude multiplication, then another control can make fine adjustments to that selection. The amplitude multiplication modification may be done in an additive fashion as shown in the example below:

Actual Amp=Amp(AD7)+Modifier(AD8).

It is noted that amplitude multiplication is used both for outer loop programming and if the outer loop system 108 is off, for the desired output of the inner loop system 102. When the outer loop system 108 is on, a normalized curve is designed which specifies the desired output over time, and an amplitude multiplier controls the amplitude of this curve. A time multiplier controls the time scale at which this curve is interpreted.

I.e.1. Command File Programming

The Output Amplitude Multiplier Algorithm controls how an output amplitude multiplier is set.

The valid exemplary selection choices are the following:

AMP_SEL_ALG_IS_KEYBOARD
AMP_SEL_ALG_IS_AD7
AMP_SEL_ALG_IS_AD8

The Output Amplitude Modifier Algorithm controls how an output amplitude modifier is set.

The valid selection exemplary choices are the following:

AMP_MODIFIER_SEL_IS_OFF
AMP_MODIFIER_SEL_IS_AD7
AMP_MODIFIER_SEL_IS_AD8

I.d. RF Activation Control

The control loop system 100 can be programmed to activate RF output based on either AD7 or AD8 inputs. A user input device, such as footswitch of the electrosurgical generator system 200 can also be used to activate RF output. The threshold of activation can be programmed.

I.d.1. Command File Programming

RF Activation Programming selects which source will start the RF activation:

RF_ACT_IS_FOOTSWITCH -Normal footswitch activation.
RF_ACT_IS_AD7 -Activated by AD7 voltage above threshold.
RF_ACT_IS_AD8 -Activated by AD8 voltage above threshold.
RF_ACT_VOLTAGE_THRESHOLD -Specifies the voltage threshold It is noted that in a preferred embodiment, footswitch activation of the electrosurgical generator system 200 is always active, even if inputs AD7 or AD8 are selected.

I.e. AD7/AD8 Curves

The programming of sensor input controls is accomplished through the creation of a "map" which specifies the amplitude multiplier and configuration index and maps these values to an input voltage.

I.e.1. Command File Programming

The Mode Control and Amplitude Multiplier Control Maps for each Control Voltage (AD7/AD8) need to be specified.

An exemplary table is shown:

| Sensor Voltage | Amplitude Multiplier | Configuration Index |
|---|---|---|
| 1.0 | 0.9 | 1 |
| 2.0 | 1.1 | 2 |

Exemplary valid programming commands are:

| #AD7_MAP_V_x | y | |
| #AD7_MAP_AMP_x | y | |
| #AD7_MAP_INDEX_x | | y |
| #AD8_MAP_V_x | y | |
| #AD8_MAP_AMP_x | y | |
| #AD8_MAP_INDEX_x | | y |
| where x = 0 - 7 | | |
| where y is the programmed value | | |

Example for AD8:

| #AD8_MAP_V_0 | 1.47 | |
| #AD8_MAP_AMP_0 | 0.0 | |
| #AD8_MAP_INDEX_0 | | 0 |
| #AD8_MAP_V_1 | 1.57 | |
| #AD8_MAP_AMP_1 | 0.0 | |
| #AD8_MAP_INDEX_1 | | 0 |
| #AD8_MAP_V_2 | 1.66 | |
| #AD8_MAP_AMP_2 | 0.0 | |
| #AD8_MAP_INDEX_2 | | 0 |

-continued

| | | |
|---|---|---|
| #AD8_MAP_V_3 | 1.76 | |
| #AD8_MAP_AMP_3 | 0.0 | |
| #AD8_MAP_INDEX_3 | | 0 |
| #AD8_MAP_V_4 | 1.85 | |
| #AD8_MAP_AMP_4 | 0.0 | |
| #AD8_MAP_INDEX_4 | | 0 |
| #AD8_MAP_V_5 | 1.94 | |
| #AD8_MAP_AMP_5 | 0.0 | |
| #AD8_MAP_INDEX_5 | | 0 |
| #AD8_MAP_V_6 | 2.04 | |
| #AD8_MAP_AMP_6 | 0.0 | |
| #AD8_MAP_INDEX_6 | | 0 |
| #AD8_MAP_V_7 | 6.00 | |
| #AD8_MAP_AMP_7 | 0.0 | |
| #AD8_MAP_INDEX_7 | | 0 |

I.e.2. Related Routines

```
894 HOST.CPP          37 |--Process_Sensor_Control
  | |
1313 HOST.CPP         38 | |--Get_AD7_Sensor_Map_Index
  | |
1343 HOST.CPP         39 | |--Get_AD8_Sensor_Map_Index
  | |
1427 HOST.CPP         40 | |--Update_Sensor_Pads
   41 | | |..sqrt
  | |
709 HOST_I~1.CPP      42 | |--Send_TCL_Data
926 HOST_I~1.CPP      43 | | |--Delay { 11 }
   44 | | |..SET_DATA_IN
  | |
646 HOST_I~1.CPP      45 | |--Get_Keying_Request
   46 | | |..DIG_In_Prt
  | |
   47 | |..AI_VRead printf
```

II. Outer Loop System

The outer loop system 108 is responsible for controlling the setpoint (e.g. DSP_Shared_Data.RF_Desired_Output) for the inner loop system 102. The concept of temperature control will be used to describe how this is accomplished, however other control methods may be used, such as but not limited to rate of change of temperature control, impedance control and rate of change of impedance control. In temperature control mode, the outer loop system 108 is programmed to follow a specific temperature vs. time curve. The outer loop system 108 uses the temperature versus time curve to retrieve its target temperature after lapse of a specified time, e.g., after a procedure has started. If the temperature is low, then the outer loop system 108 raises the inner loop setpoint. If the temperature is high, then the outer loop system 108 lowers the inner loop setpoint. The inner loop system 102 then attempts to deliver RF as specified by the inner loop setpoint, and thus raise or lower the temperature.

The user is given control of the amplitude multiplier and/or the time multiplier which adjust the temperature versus time curves. The curves are specified as normalized values from 0.0 to 1.0. Thus, the temperature curve can be increased by increasing the amplitude multiplier:

Target Temperature=Temperature_Curve(Time)*Amplitude Multiplier;

The time scale in which the curve is executed may also be adjusted by modifying the time multiplier in a similar fashion to the target temperature, thus:

Time=Time Curve*Time Multiplier;

The outer loop system 108 operates in selectable modes for controlling temperature, rate of change of impedance and work (in Joules). The source code enables the addition of other modes, if desired.

The outer loop system 108 can also be turned off. In this case, the amplitude multiplier is passed directly to the inner loop system 102 as the setpoint and the time multiplier is not used.

Sitting on top of all the outer loop modes and algorithms is a pulsing control system. This pulsing control system allows the user to specify pulsing waveform pattern parameters, such as the number of pulses in a burst of pulses, the duty cycle (e.g., ratio of on time to off time), delay time (e.g., time between bursts of pulses), frequency (e.g., 1/time between rising edges of 'on time'), and on/off amplitude envelope (e.g., amplitude pattern of a burst of pulses) for pulses to be delivered.

II.a. Command File Programming

Outer loop Proportional Integral Derivative (PID) parameters control the dynamic behavior of the outer loop system 108. Preferably, the control system is a PID system.

| | |
|---|---|
| #OUTER_LOOP_P | 1.0 |
| #OUTER_LOOP_I | 0.0001 |
| #OUTER_LOOP_D | 0.0 |

Outer loop control output limit parameters, including minimum and maximum inner loop target values, are used to limit the range that the outer loop system 108 can change the inner loop setpoint. The outer loop control output limit parameters are sent from the outer loop system 108 to the inner loop system 102. The data is either in watts, amps or volts depending on the inner loop programming (e.g., using curves selected from I, P, V curves).

Exemplary limits are:

| | |
|---|---|
| #OUTER_LOOP_OUTPUT_MAX | 150.0 |
| #OUTER_LOOP_OUTPUT_MIN | 0.0 |

An outer loop start point is the starting inner loop target. This gives the outer loop system 108 a point at which to start prior to starting active control.

An exemplary start point is:

OUTER LOOP_OUTPUT_START 5.0

Outer loop curve types specify which outer loop algorithm is to be executed. The software system may support numerous different algorithms. A few exemplary valid types are shown below:

Valid types are:

| |
|---|
| #OUTER_LOOP_ALG_IS_TEMPERATURE |
| #OUTER_LOOP_ALG_IS_OFF |

An outer loop amplitude curve specifies the target amplitude part of the target versus time curve that the outer loop system 108 uses to determine its target.

A corresponding table is provided which specifies the shape of the amplitude curve. The target value=OUTER_LOOP_CURVE_AMP [TIME*TIME_Multiptier]*AMPLITUDE_Multiplier

OUTER_LOOP_CURVE_AMP_03 0.01

Exemplary Amplitude Curve:

```
#OUTER_LOOP_CURVE_AMP_00 0.2
#OUTER_LOOP_CURVE_AMP_01 0.4
#OUTER_LOOP_CURVE_AMP_02 0.6
#OUTER_LOOP_CURVE_AMP_03 0.8
#OUTER_LOOP_CURVE_AMP_04 1.0
#OUTER_LOOP_CURVE_AMP_05 1.0
#OUTER_LOOP_CURVE_AMP_06 1.0
#OUTER_LOOP_CURVE_AMP_07 1.0
#OUTER_LOOP_CURVE_AMP_08 1.0
#OUTER_LOOP_CURVE_AMP_09 1.0
#OUTER_LOOP_CURVE_AMP_10 1.0
#OUTER_LOOP_CURVE_AMP_11 1.0
#OUTER_LOOP_CURVE_AMP_12 1.0
#OUTER_LOOP_CURVE_AMP_13 1.0
#OUTER_LOOP_CURVE_AMP_14 1.0
#OUTER_LOOP_CURVE_AMP_15 1.0
#OUTER_LOOP_CURVE_AMP_16 1.0
#OUTER_LOOP_CURVE_AMP_17 1.0
#OUTER_LOOP_CURVE_AMP_18 1.0
#OUTER_LOOP_CURVE_AMP_19 1.0
#OUTER_LOOP_CURVE_AMP_20 1.0
#OUTER_LOOP_CURVE_AMP_21 1.0
#OUTER_LOOP_CURVE_AMP_22 1.0
#OUTER_LOOP_CURVE_AMP_23 1.0
#OUTER_LOOP_CURVE_AMP_24 1.0
```

Outer loop time curve parameters specify the shape of the time curve, where each location in the OUTER_LOOP_CURVE_AMP[ ] corresponds to the values in the time curve.

The time multiplier thus allows the user to expand or contract the time at which the AMP curve generates the targets to the outer loop.

It is noted that the location may be specified with two digits, for example:

OUTER_LOOP_CURVE_TIME_03 0.01

Exemplary Time Curve:

```
#OUTER_LOOP_CURVE_TIME_00 0.0
#OUTER_LOOP_CURVE_TIME_01 0.04167
#OUTER_LOOP_CURVE_TIME_02 0.08333
#OUTER_LOOP_CURVE_TIME_03 0.125
#OUTER_LOOP_CURVE_TIME_04 0.1667
#OUTER_LOOP_CURVE_TIME_05 0.2083
#OUTER_LOOP_CURVE_TIME_06 0.25
#OUTER_LOOP_CURVE_TIME_07 0.29167
#OUTER_LOOP_CURVE_TIME_08 0.3333
#OUTER_LOOP_CURVE_TIME_09 0.375
#OUTER_LOOP_CURVE_TIME_10 0.41667
#OUTER_LOOP_CURVE_TIME_11 0.4583
#OUTER_LOOP_CURVE_TIME_12 0.5
#OUTER_LOOP_CURVE_TIME_13 0.54167
#OUTER_LOOP_CURVE_TIME_14 0.5833
#OUTER_LOOP_CURVE_TIME_15 0.625
#OUTER_LOOP_CURVE_TIME_16 0.6667
#OUTER_LOOP_CURVE_TIME_17 0.70833
#OUTER_LOOP_CURVE_TIME_18 0.75
#OUTER_LOOP_CURVE_TIME_19 0.79167
#OUTER_LOOP_CURVE_TIME_20 0.8333
#OUTER_LOOP_CURVE_TIME_21 0.875
#OUTER_LOOP_CURVE_TIME_22 0.9167
#OUTER_LOOP_CURVE_TIME_23 0.9583
#OUTER_LOOP_CURVE_TIME_24 1.0
```

Outer_Loop_Misc_Parms is an array of parameters which may be passed to the outer loop system 108 to make modifications in the algorithm, providing a method for making subtle adjustments to an algorithm for different tissue types or handsets.

A miscellaneous outer loop algorithm parameter table is for sub-variations within a specific algorithm structured as a two dimensional array, Outer_Loop_Misc_Parm[y][x].

OUTER_LOOP_MISC_PARMS_00_00 10.0

Pulse modes of the outer loop system 108 are programmed with the following exemplary commands:

Turning ON or OFF the pulse mode is accomplished with the commands:

```
#PULSE_MODE_ON
#PULSE_MODE_OFF
```

Specifying the pulse on/off widths in seconds is accomplished with the commands:

```
#PULSE_ON_WIDTH    0.100    // 100 ms
#PULSE_OFF_WIDTH   0.200    // 200 ms
```

The number of pulses to be delivered is specified by the command:

```
#NUM_PULSES    5    // 5 pulses
```

The output level (in units of the inner loop desired output) is specified by the command:

```
#PULSE_OFF_LEVEL    7    // 7 watts if constant power
```

III. Inner Loop System

The inner loop system 102 is responsible for the low level control of the RF delivery. The inner loop system 102 has programming controls for the control variable selection (e.g., current, power or voltage control), control curve definition (e.g., power curve shape), waveform definition, RF Frequency selection, calibration, sensor variable gain dynamics (e.g., automatic gain control dynamics for the V, I sensors 104) and control dynamics (e.g., HD variables for the control system).

The inner loop system 102 can be programmed for two basic modes of operation, open loop and closed loop. In open loop mode, the RF output is set to the fixed value of the high voltage power supply, and is not adjusted by software. The calibration of output RF power is controlled by Econ_Gain and Offset parameters, and the power curve is defined by the RF stage characteristics. In closed loop mode, the software reads the sensor board values of V, VI phase shift and I, and calculates Vrms, Irms, Pavg (which may be determined in accordance with the VI phase shift, Zrms, crest factor, cable impedances, Vpeak, and/or Ipeak and controls the RF output to match the desired control curve.

III.a. Command File Programming

Inner loop commands are typically specified in an 'Inner Loop' command file so that the commands are separate from the 'Outer Loop' and 'Meta' commands files. This configuration allows easier sharing of command file programming.

III.a.1. RF Frequency Selection

The system may have various RF frequency selections available such as: 250, 500, 750, 1000, 1250, 1500, 1750, 2000 Khz.

Exemplary command file programming commands for frequency selection are as follows:

```
#SET_FREQ_SEL_250KHZ
#SET_FREQ_SEL_500KHZ
#SET_FREQ_SEL_750KHZ
#SET_FREQ_SEL_1000KHZ
#SET_FREQ_SEL_1250KHZ
#SET_FREQ_SEL_1500KHZ
#SET_FREQ_SEL_1750KHZ
#SET_FREQ_SEL_2000KHZ
```

III.a.2. PID Parameters

The inner loop control dynamics are controlled by two sets of parameters, the PID parameters and the I, P, V gain adjusts. The PID parameters are adjusted to give the appropriate dynamic response assuming a system gain of 1. The I, P and/or V gain adjusts are used to modify the PID parameters based on the actual gains of the system in the respective control area (e.g., current, power and voltage) which changes based on load impedance, frequency, and waveform duty cycle.

Exemplary PID parameter commands are:

```
#CNTL_SYS_P 0.8269
#CNTL_SYS_I 0.7133
#CNTL_SYS_D 0.0264
```

Control system target gain compensation controls the change in loop gain based on which target the control system is aiming at (e.g., current, power, voltage). The PID_GAIN_ADJ is multiplied by the PID values to change the loop gain, e.g., P=CNTL_SYS_P*I_PID_GAIN_ADJ.

Exemplary Gain Adjust parameter commands are:

```
#I_PID_GAIN_ADJ    0.3
#P_PID_GAIN_ADJ    0.008
#V_PID_GAIN_ADJ    0.005
```

III.a.3. Crest Factor

Crest factor is defined as: Crest Factor=Pk/Rms. Crest factor specifies the ratio of the signal PK to RMS value, thus giving an indication of maximum amplitude to be expected from the waveform.

Since the system reads the actual V, I waveforms, the software needs to know how to set the scaling for sensors on a sensor board for the specified waveform. Crest factor allows the software to calculate the maximum expected amplitude of the waveform, so that it can calculate the PID settings for the sensor board.

The crest factor should be measured at about 10 ohms, which is typically the highest (e.g., corresponds to the least ringing).

An exemplary crest factor setting command is:

CREST_FACTOR 2

III.a.4. Control Mode/Curve Definitions

A control mode definition specifies which basic mode the control system operates in, open or closed loop.

Exemplary control mode definition commands are:

```
#CONTROL_MODE_IS_OPEN_LOOP
#CONTROL_MODE_IS_CLOSED_LOOP
```

A control curve definition specifies how the impedance curve maps are interpreted.

Exemplary control curve definition commands are:

```
#CONTROL_CURVE_IS_CURRENT
#CONTROL_CURVE_IS_POWER
#CONTROL_CURVE_IS_VOLTAGE
```

III.a.5. Control System Maximums

Control system maximum parameters control the maximum outputs allowed for the generator in the given mode. This protects the generator, as the control system does not allow the current, power, and/or voltage to go beyond these limits no matter what other settings are programmed to be set to. Current is in RMS Amps, power in watts, and voltage is in RMS volts.

Exemplary maximum parameter control commands are:

```
#MAX_CURRENT 4.0
#MAX_POWER    150
#MAX VOLTAGE 500
```

III.a.6. Control Curve Definition

An RF output control curve can be programmed to one of at least three modes of operation: constant current, constant power and constant voltage.

The modes of operation specify the target that the control system tries to control. All of these modes use two maps (e.g., the curve map and the impedance map) and the Zlow and Zhigh parameters to define the operation. Viewed together these two maps define the basic shape of the control curve at the specified impedance points. Preferably, the curve map is normalized from 0 to 1.0 and the impedance map is in ohms.

Exemplary maps can be viewed as below:

| Impedance Map Value | Curve Map Value |
| --- | --- |
| 0 | 0.5 |
| 100 | 0.75 |
| 200 | 1.0 |
| 300 | 1.0 |
| 500 | 0.5 |

A curve defined by the exemplary map value is shown in FIG. 2A. Exemplary charts of each mode are shown in FIGS. 2B-2D and explained below.

III.a.6.i. Constant Current Curves

The constant current mode attempts to provide constant current from 0 to Z High ohms. After Z High ohms, it switches to providing constant voltage (see FIG. 2B).

III.a.6.ii. Constant Power Curves

The constant power mode attempts to provide constant power from Z Low to Z High ohms. Below Z Low, it switches to providing constant current mode, and above Z High, it switches to providing constant voltage (see FIG. 2C).

III.a.6.iii. Constant Voltage Curves

The constant voltage mode attempts to provide constant voltage from Z Low and above. Below Z Low, it switches to providing constant current (see FIG. 2D).

III.a.7. Sensor Automatic Gain Control Dynamics

To accurately read the voltage and current sensors 104, an automatic gain control system is provided to the electrosurgical generator system 200 for providing a high speed A/D converter with a properly amplified signal. The dynamics of this gain control are programmed as a PID controller. The commands for programming the PID controller are as follows:

```
#V_SENSOR_VGAIN_P    0.002    //Voltage Var Gain P
#V_SENSOR_VGAIN_I    0.004    //Voltage Var Gain I
#V_SENSOR_VGAIN_D    0.0      //Voltage Var Gain D
#I_SENSOR_VGAIN_P    0.002    //Current Var Gain P
#I_SENSOR_VGAIN_I    0.004    //Current Var Gain I
#I_SENSOR_VGAIN_D    0.0      //Current Var Gain D
```

III.a.8. Waveform Definition

The RF waveform is defined by a pulse generator which activates the main RF stage (e.g., FETs). The programming of the pulse generator allows specification of at least the pulse width, the number of pulses and an off time. This allows a wide variety of waveform patterns to be programmed for the electrosurgical generator system 200.

III.a.9. Outer Loop

One embodiment of the present disclosure includes splitting the outer loop system into two sub-sections: an outer loop target generator which handles the time-based changes to the setpoint of the outer loop (e.g., temperature versus time curves) and an inner loop target generator which selects which target (e.g., voltage, current, power) the inner loop is controlling.

III.a.10 Downloading Configuration Files

It is contemplated that the system of the present disclosure can be configured such that the system allows the downloading of the configuration files into the electrosurgical generator by the user. The new configuration files could be purchased or given to the user for upgrading the electrosurgical system.

Figure 3:
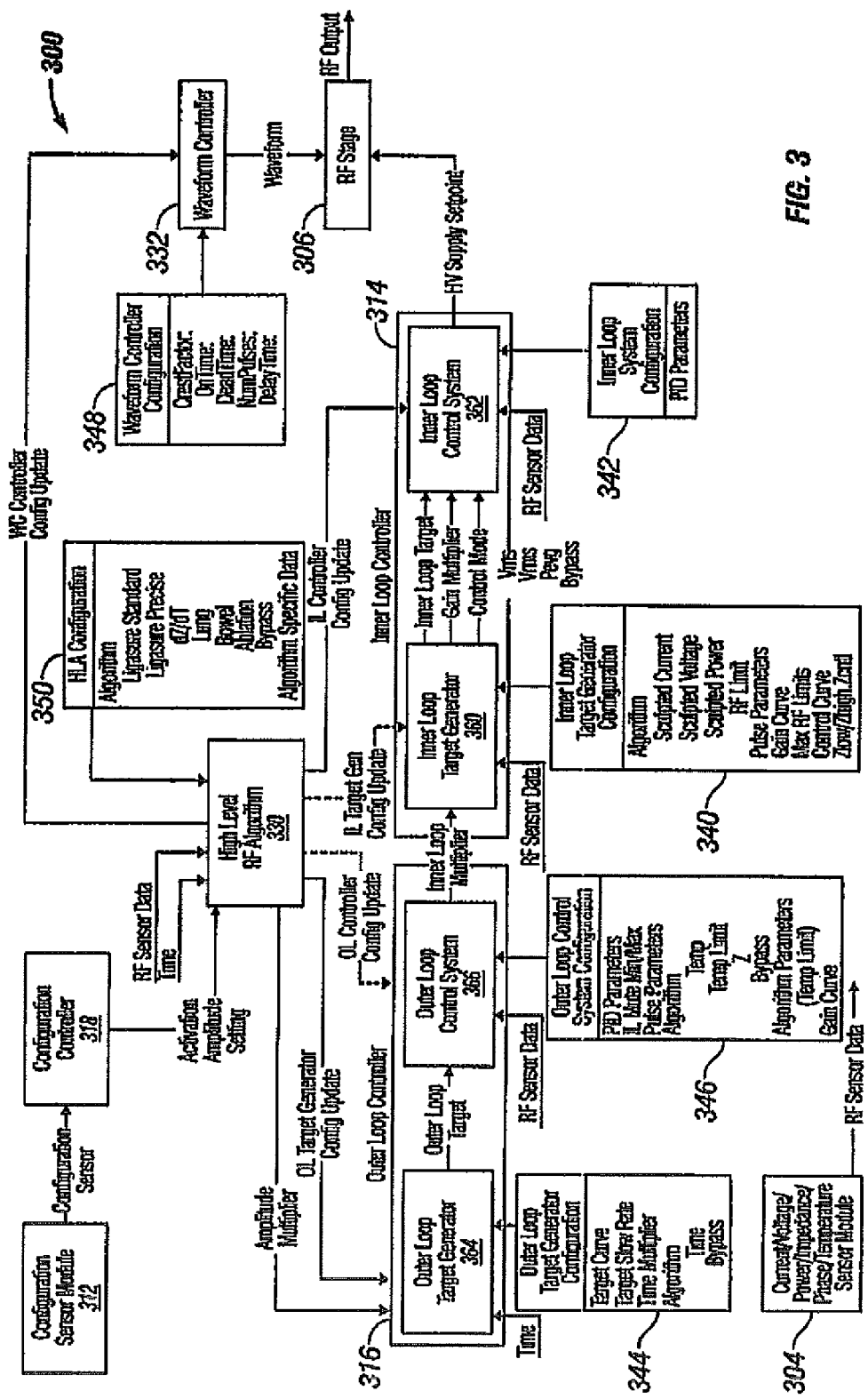
FIG. 3 is a block diagram of a control loop system of an electrosurgical generator in accordance with another embodiment of the invention.

FIG. 3 shows another embodiment of the electrosurgical generator system, designated generally by the number 300. An inner loop controller 314 includes at least the functionality of the inner loop controller 114 shown in FIG. 1. An outer loop controller 316 together with a high level RF algorithm (HLA) module 330 include at least the functionality of the outer loop controller 116 shown in FIG. 1. A control system for an electrosurgical generator having an inner and outer loop controller is described in U.S. patent application Ser. No. 10/427,832, filed on May 1, 2003, the contents of which are incorporated herein by reference in their entirety. A configuration controller 318 includes at least the functionality of the configuration controller 118 shown in FIG. 1. A sensor module 304 includes at least the sensors 104 shown in FIG. 1 and a configuration sensor module 312 includes at least the sensors 112 shown in FIG. 1. An RF stage 306 corresponds to the RF stage 106 shown in FIG. 1. A waveform pattern controller 332 provides at least functionality described above with respect to waveform generation.

Configuration data 340, 342, 344, 346, 348 350 is generated by the configuration controller 318. The inner loop controller 314 includes an inner loop target generator (ILTG) 360 and an inner loop control module (ILCM) 362. The outer loop controller 316 includes an outer loop target generator (OLTG) 364 and an outer loop control module (OLCM) 366. The ILTG configuration data 340 is provided to the ILTG 360. The ILCM configuration data 342 is provided to the OLCM 366. The OLTG configuration data 344 is provided to the OLTG 364, the OLCM configuration data 346 is provided to the OLCM 366. The waveform controller configuration data 348 is provided to the waveform controller 332. The HLA module configuration data 350 is provided to the HLA module 330.

The elements ILTG 360, ILCM 362, OLTG 364, OLCM 366, the configuration controller 318, the configuration sensor module 312, the HLA module 330, the waveform controller 332 or the sensor module 304, or a combination thereof, may be disabled and/or bypassed, or a connection between two or more elements may be disabled so that the electrosurgical generator control system 300 may operate without the disabled element. The disabled elements pass the input directly to the output of the module, thus allowing the enabled elements to operate with no change from the disabled units. The inner loop controller 314 processes sensor data received from the sensor module 304 in accordance with configuration data received from the configuration controller 318, updated configuration data received from the HLA module 330, and the inner loop multiplier control signal received from the outer loop controller 316, and generates a supply setpoint control signal which is provided to the RF stage 306, where an amplitude of an aspect of the RF energy output by the RF stage 306 is controlled in accordance with the supply setpoint. In the example provided in FIG. 3, the supply setpoint is an HV supply setpoint which controls amplitude of the voltage output by the RF stage 306.

The ILTG 360 receives configuration data including at least one algorithm selected from algorithms including a sculpted curve (including sculpted current, sculpted voltage and sculpted power) and RF limit algorithms, pulse parameters (pulse enable (for enabling or disabling pulsing function), pulse on (length of "high" pulse), pulse off (length of "low" pulse), pulse min (amplitude of "low" pulse), an inner loop gain curve, maximum RF limits, a control curve and Zlow, Zhigh, And values (where Zcntl indicates when to switch the control variable, e.g., from current to voltage, or vice versa); sensor data from the sensor module 304; and the inner loop multiplier from the outer loop controller 316. The ILTG 360 generates a target signal to the ILCM 362 based on the inner loop control curve provided via the configuration data from the configuration controller 318 and updatable by the configuration update data from the HLA module 330; the inner loop multiplier from the outer loop controller 316; and impedance and actual RF current and voltage from the sensor module 304. The target signal preferably represents voltage, but it can also represent the HV supply setpoint in the case when the ILCM is bypassed and/or disabled.

The ILTG 360 further includes modules for performing the following functions: performing a sculpted curve algorithm including, for example, but not limited to converting a sculpted current or power control curve into a voltage control curve; limiting the control curve to the maximum values (e.g., for current, voltage and power) allowed for the hardware; calculating and generating the inner loop target based on the sensor data, the control curve and the inner loop multiplier; controlling the inner loop control module gains based on impedance sensor data and the gain curve which specifies changes in gain due to changes in impedance for generating the gain multiplier; pulsing the inner loop target; and selecting a mode based on the sensed load impedance and the impedance breakpoints Zlow, Zhigh and Zcntl, and generating a control mode signal in accordance with the selected mode.

Mode selection determines which sensor data is to be used by the ILCM 362 and which variable is to be controlled, e.g., sensor data that corresponds to current, voltage or power for controlling current, voltage or power, respectively. Preferably, current control is to be used for impedances less than Zlow, power or voltage control is used for impedance values between Zlow and Zhigh, and voltage control is used for the remaining impedance values. To avoid inaccuracy and prevent unnecessary control mode switching when the impedance is near a breakpoint, hysteresis is used when the impedance is close to a breakpoint.

The RF limit algorithm causes the ILTG 360 and the ILCM 362 to operate in an open loop mode in which there is minimal software control of the HV supply setpoint output in response to sensor data. The open loop mode is generally used for calibration and service functions, but is not limited thereto. Preferably, in the open loop mode the amplitude activation setting determines the percentage of full scale output that the RF stage 306 will deliver. The RF limit algorithm protects the RF stage 306 from user actions, such as setting the activation amplitude setting to a level that could cause the HV supply setpoint to be set to a level that could damage the RF stage 306. The HV supply setpoint is kept within predetermined limits, where the limits are determined by the control curve.

The inner loop control curve is interpreted to represent the maximum allowed HV supply setpoint at the specified impedance (Z). As long as the maximum HV supply setpoint allowed is not exceeded, as defined by the inner loop control curve, control of the HV supply setpoint is based on the inner loop multiplier. If the control curve is exceeded, then the output HV supply setpoint is held at the maximum allowed HV supply setpoint for providing protection to the electrosurgical unit receiving the energy generated by the RF stage 306. The HV supply setpoint is set to equal the inner loop multiplier after the HV supply setpoint is less than the maximum RF limit value, with some possible hysteresis.

The max RF limits parameter provides another layer of control layered on top of the control curve for use with any algorithm by providing maximum limits for current, voltage and/or power levels of the HV supply setpoint. The control layer which uses the max RF limits parameter further provides protection to the RF stage unit 306 and the electrosurgical unit (ESU) receiving the energy generated by the RF stage 306, including protection from changes to the software. Furthermore, the control system may use the minimum of the limits described by the control curve and the max RF limit for limiting the HV supply setpoint.

The pulsing function may run in parallel with other ILTG 360 algorithms. The duration of the "high" and "low" pulses, the time between leading edges, the level for the "low" pulse, etc., are specified by the pulse parameters. The level for the "high" pulse is defined by the control curve, the impedance data from the sensor data and the inner loop multiplier for closed loop control, or by the inner loop multiplier for open loop control, such as when the RF limit algorithm is performed. The pulsing of the inner loop target may contribute to providing sharp edged pulses of the HV supply setpoint, if desired.

The inner loop control curve received via the configuration data specifies the inner loop desired output values versus sensed impedance values obtained from sensor data. The desired output values of the received inner loop control curve represent current, voltage or power, as determined by the algorithm received via the configuration data (e.g., the sculpted current, voltage or power algorithm, respectively). The received inner loop control curve may be converted into a voltage, current or power curve, in accordance with the mode selected, in which the desired output values represent voltage, current or power, respectively. The control curve (or converted control curve) may be structured, for example, as a multi-dimensional array. One column of the array specifies impedance values, and another column specifies desired output values, where the desired output values represent current, power or voltage in accordance with the control mode. Preferably the desired output values are normalized between 0 and 1.0. A desired output value which is output as the inner loop target is generated by obtaining a normalized desired output value via linear interpolation based on the actual impedance, and multiplying the normalized desired output value by the inner loop multiplier.

Control of the inner loop control module gains (herein referred to as inner loop gain control) includes generating the gain multiplier in response to a constant control voltage as impedance changes. System gain (e.g., RF voltage/HV supply set-point, where the RF voltage is measured RF voltage output by the RF stage 306) varies with patient load impedance. The inner loop gain control objective is to stabilize the system gain to keep it close to constant as the load impedance changes. The inner loop gain curve is theoretically a set of points of a gain multiplier plotted versus impedance derived from the design of the hardware, which is designed to adjust the gains due to the response of the electrosurgical generator system 300.

The gain curve preferably holds a normalized voltage response versus impedance. By using a normalized voltage response, the voltage is converted into the variable that we are controlling (current, power, or voltage). The gain multiplier is computed by taking the inverse of the voltage response that corresponds to the sensed impedance. The gain multiplier is used to adjust the inner loop PID values of the ILCM 362 so that the control system gain is close to constant. Accordingly, the PID values should be calculated assuming a system gain of 1.0, as the PID values are adjusted as described above.

To compute the gain multiplier, for voltage control, the interpolated value of the gain curve is inverted. For power control, the gain multiplier is $Z/V^2$ (where V is the interpolated value from the gain curve). For current control, the gain multiplier is $Z/V$. Accordingly, the ILSM 362 can use a single set of PID gain values for the inner loop voltage, current or power control, and the gain multiplier is used to modify the PID gains during the procedure in virtual real-time.

The ILCM 362 receives configuration data including control parameters, such as PID parameters; sensor data from the sensor module 304 and the inner loop target, the gain multiplier and the control mode (Irms, Vrms, Pavg or Bypass) from the ILTG 360. The ILCM 362 adjusts the HV supply setpoint in accordance with the received data so that the inner loop target is reached.

The ILCM 362 preferably uses a control algorithm, such as a PID algorithm, which is able to switch between control modes such as current control, voltage control, power control and a bypass mode (e.g., minimal control, where received data is provided as the output) without large disturbances when switching control modes. When the ILTG 360 is performing the RF limit algorithm, the ILCM 362 is preferably in bypass mode. When switching between control modes, the PID loop algorithm (if active) pre-loads the integral term for minimum disturbance.

With respect to the outer loop controller 316, the OLTG 364 receives configuration data including the outer loop target curve, the target slew rate, the time multiplier and an algorithm selectable from algorithms including time control or bypass algorithms; the amplitude multiplier from the HLA module 330; and time signals. Other than when performing the bypass algorithm, the OLTG 364 generates a time varying outer loop target in accordance with the received data which is provided to the OLCM 366, where the outer loop target may represent a property such as, but not limited to, temperature, current, power, voltage or impedance. Preferably, the outer loop target is generated by a linear interpolation of the adjusted outer loop target curve, where the target curve provided via the OLTG configuration data is adjusted in accordance with the amplitude multiplier, the time multiplier and/or time.

The outer loop target slew rate parameter allows the system to have a programmable slew rate of the outer loop target, so that regardless of how quickly the amplitude multiplier changes, the outer loop target will not change faster than the programmed slew rate. The outer loop target slew rate control function is typically used in systems in which the user may have direct control of a parameter, such as the activation amplitude setting, and it is desired to limit the rate at which the activation amplitude setting can be changed.

The OLCM 366 receives configuration data including control parameters, such as PID parameters, inner loop multiplier maximum and minimum limit values, pulse parameters, at least one algorithm selectable from algorithms such as temperature, temperature limit, impedance (Z), or bypass algorithms, algorithm parameters, such as temperature limits and an outer loop gain curve; sensor data from the sensor module 304 and the outer loop target from the OLTG 364. Preferably, the OLCM 366 uses a control algorithm, such as a PID algorithm which operates in accordance with the PID parameters. The OLCM 366 adjusts the inner loop multiplier in accordance with the received data in order to reach the outer loop target.

The OLCM 366 is capable of pulsing the inner loop multiplier. When the pulse is "on", the output value is the computed inner loop multiplier. When the pulse is "off", the output is set to a predetermined value.

The OLCM 366 controls outer loop gain. The outer loop gain curve describes a plot of gain multiplier versus impedance derived from the inner loop control curve, and thus the programming of the inner loop by way of the configuration parameters. The outer loop gain curve may be structured, for example, as a two-dimensional array. When outer loop gain control is enabled, the outer loop gain is multiplied by the gain multiplier that corresponds to the received impedance sensor data. The outer loop gain control stabilizes the system gain to maintain system gain that is close to constant. From the perspective of the outer loop controller 316, the system gain varies with patient load impedance due to the inner loop control curve programming. Conceptually, the outer loop gain is multiplied by the inverse of the normalized inner loop control curve, thus keeping the system gain close to constant. The outer loop gain curve specifies the inverse of the normalized inner loop control curve, where the outer loop gain curve may be further adjusted for keeping the system stable.

The HLA module 330 receives configuration data including at least one procedural algorithm selectable from algorithms for controlling the electrosurgical generator system 300 during specific types of procedures, or procedures performed under specific conditions, such as on specific organs. The procedural algorithms include algorithms, such as, vessel sealing (e.g., LigaSure™ (standard and precise)), rate of change of impedance (dZ/dt), lung, bowel, ablation, etc., and bypass algorithms, and a combination thereof; algorithm specific data for adjusting at least one specified procedural algorithm; sensor data from the sensor module 304; time signals; user entered settings; and the activation amplitude setting from the configuration controller 318.

Preferably, the HLA module 330 uses a state based control algorithm. The HLA module 330 performs top level RF delivery algorithms which are primarily state based. The HLA module 330 has the capability of changing the configuration data of the lower level modules, including the ILTG 360, the ILCM 362, the OLTG 364 and the OLCM 366 and the waveform controller (332). The HLA module 330 sets up the lower level modules in accordance with the received data by adjusting the corresponding configuration data as determined necessary. Furthermore, during a procedure the HLA module 330 reprograms the lower level modules in accordance with the received data by adjusting the corresponding configuration data in accordance with the algorithm selected, and in response to measured properties as indicated by the received sensor data, where the reprogramming may be performed in virtual real-time.

The user entered settings may be used in conjunction with any of the algorithms selected. Furthermore, the user entered settings may control the activation amplitude setting for one or more electrical or physical properties (e.g., power, current, voltage or temperature) without directly identifying the particular property and target setting. For example, the user may select from a variety of generic settings, where each generic setting includes a predetermined setting for one or more properties.

The waveform controller 332 receives configuration data including "on" time, dead time, number of pulses per burst of pulses, and delay time between bursts of pulses. It is contemplated that the waveform controller 332 may be programmed by the HLA module 332 if determined necessary, and/or by the configuration file via download from the configuration controller 318. The waveform controller 332 controls the hardware which generates a wave pattern (such as a square wave pattern) which drives FETs in the RF stage. Parameters of the waveform pattern that may be controlled by the waveform controller 332 include at least, "on" time (pulse width of a single pulse), dead time (delay to next pulse), number of pulses per group of pulses, and delay time between groups of pulses.

The waveform generator 332 may receive an amplitude envelope parameter with the configuration parameters, and may further include circuitry, such as analog and/or logic circuitry for adjusting amplitude of pulses within a burst of pulses. The amplitude envelope parameter may describe the amplitude setting for individual pulses of groups (or bursts) of pulses. The amplitude adjustments may be performed at a rate that is faster than the rate at which the software, such as the inner loop controller 314, is capable of providing control, so that the amplitude adjustments may be provided for individual pulses of groups of pulses. The waveform generator may receive a control signal, such as a control signal from the ILCM 362, indicative of the HV supply setpoint, for synchronizing the amplitude adjustments with the HV supply setpoint or with the signals output by the RF stage 106.

Preferably, the configuration controller 318 is a system which selects the required configuration files based on user input and download them to the rest of the system. It is contemplated that the configuration controller 318 may be removable and replaceable. The configuration controller receives configuration sensor data from the configuration sensor module 312 and/or user input devices (not shown) for direct user input. The configuration controller 318 generates the configuration data and the activation amplitude setting in accordance with the received data. The configuration controller 318 selects the algorithm to be used by the ILTG 360, OLTG 364, OLCM 366 and the HLA 330. The configuration data is provided to the appropriate modules as described above, and the activation amplitude setting is provided to the HLA module 330.

The configuration controller may configure itself (or alternatively be configured by another processor) in accordance with conditions, such as the ESU and/or the user interface to the electrosurgical generator system being used.

The configuration sensor module 312 includes sensors for sensing user actions, (including user actions not intentionally related to providing input to the configuration controller 318), environmental conditions, patient conditions or other properties or conditions. The configuration sensor module 312 further includes analog and or digital circuitry and software modules for processing signals generated by the sensors such as for preparing the signals for input to the configuration controller 318, and for controlling the sensors.

The sensors of the configuration sensor module 312 may include, for example, a sensor for sensing adjustment of a slider mechanism on the ESU for selecting a parameter on the ESU, an optical sensor for sensing a property of the patient's tissue, a proximity sensor for sensing thickness of the patient's tissue, a motion sensor for sensing motion of the ESU or the patient, a sensor for sensing moisture levels of tissue, etc. A portion of the sensors may be provided within the sterile field of the electrosurgical procedure. The configuration sensor module 312 may further include one or more commercially available user input devices.

The sensor module 304 includes sensors for sensing electrical properties of energy as output by the electrosurgical device, and/or electrical and/or physical properties proximate the surgical site or the ESU. Furthermore, the sensor module includes analog and or digital circuitry and software modules for processing signals generated by the sensors such as for preparing the signals for input to the control system of the electrosurgical generator system 300, and for calculating values derived from the sensed properties. It is contemplated that sensors and circuitry may be shared by the sensor module 304 and the configuration controller 318. Furthermore, the sensor module 304 may further include at least one control system for controlling the sensors, amplification of sensed signals, sampling rates of the sensors, etc. The sensor module 304 may further include one or more commercially available user input devices.

In a preferred embodiment, a user may enter user input to the configuration controller for selecting (directly or indirectly) configuration parameters, the activation amplitude setting and the amplitude multiplier. As described above, the user input to the configuration controller may not be intentionally entered for selecting configuration parameters.

It is contemplated that another configuration parameter, an expected crest factor parameter, may be provided to at least one of the modules of the control system of the electrosurgical generator 300 for providing further control. Furthermore, the sensor module 304 may include sensors for sensing the crest factor. The control system may further include a safety monitor module which compares the expected crest factor parameter with the sensed crest factor, and sends control signals to other modules of the control system for making adjustments in accordance with the results of the comparison. The sensor module 304 may configure the sensors for setting up the dynamic range of the sensors in accordance with the expected crest factor parameter.

It is further contemplated that the control system includes an activation sequencer which controls startup and ending of RF delivery. The activation sequencer may receive configuration data from the configuration controller 318 and or updated configuration data from the HLA module 330 for performing startup and/or shutdown procedures in accordance with the configuration data and/or updated configuration data.

The software modules of the electrosurgical generator control system 300, including the inner loop controller 314, outer loop controller 316, the configuration controller 318, the HLA module 330, the waveform controller 332 and control modules associated with the sensor module 304 and/or the configuration sensor module 312 are respectively executable on at least one processor, such as a microprocessor and/or a DSP. Resources for processing, storage, etc., or a combination thereof may be shared by any combination of the aforementioned software modules. The software instructions of the respective software modules may be stored on computer readable medium, such as CD-ROMs or magnetic disks, and/or may be transmitted and/or received via propagated signals.

In operation, the control system may be initialized during the power up and/or the activation process. The electrosurgical generator system 300 recognizes (via sensing or "plug and play" notification) the type of ESU and/or electrosurgical generator user interface to be used. Sensors of the sensor module 304 and/or the configuration sensor module 312 sense initialization properties associated with the environment, ESU or patient. Information is entered via a user interface, such as patient and/or procedure related information (procedure to be performed, tissue to be operated upon, patient identification, age, weight, expected fat content). The information or additional information may be retrieved from a database accessible by the control system of the electrosurgical generator system 300.

The appropriate configuration files are selected or generated by the configuration controller 318. It is contemplated that at least a portion of the configuration files are stored by the configuration controller 318 and/or associated memory. Accordingly, selected configuration files not stored by the configuration controller 318 may be downloaded to the configuration controller 318 through various methods. Upon activation of the electrosurgical generator system 300 the configuration controller 318 downloads the configuration files into the respective modules of the control system.

The control system for the electrosurgical generator system 300 provides a high degree of flexibility for performing a wide variety of different types of control for controlling the output of electrosurgical energy for use in a wide variety of types of procedures which may be performed under a wide variety of circumstances. Furthermore, the control system provides a wide variety of different types of control during a procedure, where the control and selection of the type of control is provided on the fly, or in virtual real time in response to properties associated with sensed properties and/or user input or actions. The type of control provided may be selected in response to a variety of factors, such as sensed or input tissue response, type of electrosurgical instrument being used, patient profile, the type of procedure being performed, environmental conditions, the type of tissue being treated and the condition of the tissue being treated.

Although this disclosure has been described with respect to preferred embodiments, it will be readily apparent to those having ordinary skill in the art to which it appertains that changes and modifications may be made thereto without departing from the spirit or scope of the claims appended hereto.

What is claimed is:

1. A programmable electrosurgical generator system having an RF output stage for outputting at least one RF operating waveform for performing an electrosurgical procedure, the programmable electrosurgical generator comprising:
   an inner loop system configured to change at least one parameter of the at least one RF operating waveform;
   an outer loop system configured to provide at least one operating command to the inner loop system;
   a configuration control system that modifies at least one of the inner and outer loop systems based on received data from a sensor module; and
   a high level RF algorithm module configured to program at least one algorithm or an algorithm parameter for the at least one algorithm of the inner loop system or the outer loop system based on received sensor data from the sensor module that senses properties associated with the electrosurgical procedure or the output of at least one RF operating waveform.

2. The electrosurgical generator system as in claim 1, wherein the at least one parameter is selected from the group consisting of output power, output current, output voltage, and output waveform pattern.

3. The electrosurgical generator system as in claim 1, further comprising a user interface configured to input and provide to the configuration control system programming commands for operating the inner loop system, the outer loop system or the configuration control system in accordance with the programming commands.

4. The electrosurgical generator system as in claim 3, further comprising at least one memory module configured to store the inputted programming commands as command files.

5. The electrosurgical generator system as in claim 4, wherein each command file defines values of various parameters of an operating mode.

6. The electrosurgical generator system as in claim 1, wherein the sensor module having at least one sensor for sensing that senses electrical or physical properties responsive to application of the electrosurgical energy and generates sensor data corresponding to the sensing; wherein the inner loop system or the outer loop system uses the sensor data for changing and performing, respectively.

7. The electrosurgical generator system as in claim 6, wherein the at least one sensor is selected from the group consisting of current, phase shift, voltage, power, impedance, and temperature sensors.

8. The electrosurgical generator system as in claim 6, wherein the inner loop and outer loop systems use different subsets of the sensor data.

9. The electrosurgical generator system as in claim 6, further comprising at least one processor configured to create and store a plurality of operating modes for the electrosurgical generator system.

10. The electrosurgical generator system as in claim 1, wherein the configuration control system is adapted to re-program the inner and outer loop systems in virtual real-time.

11. A programmable electrosurgical generator system having an RF output stage configured to output at least one RF Operating waveform that performs an electrosurgical procedure, the programmable electrosurgical generator comprising:
   an inner loop system including means for changing at least one parameter of the at least one RF operating waveform;
   an outer loop system including means for performing at least one operating function of the electrosurgical generator;
   a configuration control system including means for modifying the inner and outer loop systems based on received input data; and
   a high level RF algorithm module configured to program an operating parameter or an operation of the inner loop system or the outer loop system based on received sensor data from a sensor module that senses properties associated with the electrosurgical procedure.

12. The electrosurgical generator system as in claim 11, wherein the at least one parameter is selected from the group consisting of output power, output current, output voltage, and output waveform pattern.

13. The electrosurgical generator system as in claim 11, wherein the at least one operating function is selected from the group consisting of receiving input information from at least one sensor, and providing at least one operating command to the means for changing the at least one parameter of the at least one operating waveform.

14. The electrosurgical generator system as in claim 11, further comprising means for receiving programming commands for operating the inner loop system, the outer loop system and the configuration control system in accordance with the programming commands, and means for inputting the programming commands.

15. The electrosurgical generator system as in claim 14, further comprising at least one memory module configured to store the inputted programming commands as command files.

16. The electrosurgical generator system as in claim 15, wherein each command file defines values of various parameters of an operating mode.

17. The electrosurgical generator system as in claim 11, wherein the sensor module having at least one sensor that senses electrical or physical properties responsive to application of the electrosurgical energy and generates sensor data corresponding to the sensing; wherein the means for changing of the inner loop system or the means for performing of the outer loop system uses the sensor data for changing and performing, respectively.

18. The electrosurgical generator system as in claim 17, wherein the at least one sensor is selected from the group consisting of current, phase shift, voltage, power, impedance, and temperature sensors.

* * * * *